(12) United States Patent
Khosravi et al.

(10) Patent No.: US 11,806,238 B2
(45) Date of Patent: Nov. 7, 2023

(54) METHODS AND APPARATUS FOR TREATING NEUROVASCULAR VENOUS OUTFLOW OBSTRUCTION

(71) Applicant: Incept, LLC, Sunnyvale, CA (US)

(72) Inventors: Fred Khosravi, Mountain View, CA (US); Gerard von Hoffmann, Rancho Santa Fe, CA (US)

(73) Assignee: Incept, LLC, Sunnyvale, CA (US)

( * ) Notice: Subject to any disclaimer, the term of this patent is extended or adjusted under 35 U.S.C. 154(b) by 409 days.

(21) Appl. No.: 17/027,368

(22) Filed: Sep. 21, 2020

(65) Prior Publication Data

US 2021/0100657 A1    Apr. 8, 2021

Related U.S. Application Data

(63) Continuation of application No. 15/589,032, filed on May 8, 2017, now Pat. No. 10,779,947, which is a
(Continued)

(51) Int. Cl.
*A61F 2/24* (2006.01)
*A61F 2/915* (2013.01)
(Continued)

(52) U.S. Cl.
CPC .......... *A61F 2/2475* (2013.01); *A61F 2/915* (2013.01); *A61M 25/104* (2013.01);
(Continued)

(58) Field of Classification Search
CPC ........ A61B 17/12009; A61F 2/01; A61F 2/95; A61F 2/958; A61F 2/0105; A61F 2/2418; A61F 2/2475; A61F 2/856; A61F 2220/0008; A61F 2220/0016; A61M 25/104; A61M 25/1011;
(Continued)

(56) References Cited

U.S. PATENT DOCUMENTS 4,198,981 A * 4/1980 Sinnreich ............... A61B 17/42
606/119
4,423,725 A    1/1984 Baran et al.
(Continued)

FOREIGN PATENT DOCUMENTS

EP         2105 110       9/2009
WO    WO 2001/056500    8/2001
(Continued)

OTHER PUBLICATIONS

Bagul et al., *Migration of superior vena cava stent*, Journal of Cardiothoracic Surgery 2008, 3:2, Mar. 10, 2008.
(Continued)

*Primary Examiner* — Jocelin C Tanner
(74) *Attorney, Agent, or Firm* — Knobbe, Martens, Olson & Bear, LLP

(57) ABSTRACT

Methods and devices are disclosed for treating neurovascular venous outflow obstructions, with or without implantation of a prosthetic valve. The valve may be carried by a support, such as a stent, which may be self-expandable or balloon expandable. Both transvascular and direct surgical access is contemplated.

20 Claims, 24 Drawing Sheets

Related U.S. Application Data continuation of application No. 14/550,748, filed on Nov. 21, 2014, now Pat. No. 9,675,457, which is a continuation of application No. 13/191,296, filed on Jul. 26, 2011, now abandoned.

(60) Provisional application No. 61/400,383, filed on Jul. 27, 2010.

(51) Int. Cl.
  *A61M 25/10* (2013.01)
  *A61F 2/856* (2013.01)
  *A61M 25/01* (2006.01)
  *A61F 2/01* (2006.01)
  *A61B 17/12* (2006.01)

(52) U.S. Cl.
  CPC .... *A61M 25/1011* (2013.01); *A61B 17/12009* (2013.01); *A61F 2/0105* (2020.05); *A61F 2/2418* (2013.01); *A61F 2/856* (2013.01); *A61F 2002/016* (2013.01); *A61F 2002/91583* (2013.01); *A61F 2220/005* (2013.01); *A61F 2220/0008* (2013.01); *A61F 2220/0016* (2013.01); *A61F 2220/0075* (2013.01); *A61F 2230/0006* (2013.01); *A61F 2230/0054* (2013.01); *A61F 2230/0067* (2013.01); *A61F 2230/0091* (2013.01); *A61F 2230/0093* (2013.01); *A61M 2025/0175* (2013.01); *A61M 2025/109* (2013.01); *A61M 2025/1015* (2013.01); *A61M 2025/1047* (2013.01); *A61M 2025/1086* (2013.01)

(58) Field of Classification Search
  CPC .. A61M 2025/0175; A61M 2025/1015; A61M 2025/1047; A61M 2025/1086; A61M 2025/109
  See application file for complete search history.

(56) References Cited

U.S. PATENT DOCUMENTS

| | | | |
|---|---|---|---|
| 5,180,367 A * | 1/1993 | Kontos | A61M 25/104 604/243 |
| 5,250,070 A * | 10/1993 | Parodi | A61M 25/104 604/103.08 |
| 5,500,014 A | 3/1996 | Quijano et al. | |
| 5,653,690 A * | 8/1997 | Booth | A61M 25/04 604/103.07 |
| 5,665,063 A * | 9/1997 | Roth | A61F 2/82 604/509 |
| 5,820,595 A * | 10/1998 | Parodi | A61F 2/958 604/101.05 |
| 5,972,029 A | 10/1999 | Fuisz | |
| 5,997,573 A | 12/1999 | Quijano et al. | |
| 6,019,789 A | 2/2000 | Dinh et al. | |
| 6,299,637 B1 | 10/2001 | Shaolian et al. | |
| 6,336,937 B1 | 1/2002 | Vonesh et al. | |
| 6,350,277 B1 | 2/2002 | Kocur | |
| 6,613,077 B2 | 9/2003 | Gilligan et al. | |
| 6,663,664 B1 | 12/2003 | Pacetti | |
| 6,706,013 B1 * | 3/2004 | Bhat | A61M 25/1011 606/101 |
| 6,758,858 B2 | 7/2004 | McCrea et al. | |
| 7,022,132 B2 | 4/2006 | Kocur | |
| 7,449,027 B2 | 11/2008 | Hunt | |
| 7,468,071 B2 | 12/2008 | Edwin et al. | |
| 7,871,434 B2 | 1/2011 | Case | |
| 8,562,672 B2 | 10/2013 | Bonhoeffer et al. | |
| 2001/0053929 A1 | 12/2001 | Vonesh et al. | |
| 2002/0177894 A1 | 11/2002 | Acosta et al. | |
| 2003/0055492 A1 | 3/2003 | Shaolian et al. | |
| 2004/0034407 A1 * | 2/2004 | Sherry | A61F 2/848 623/1.15 |
| 2004/0167619 A1 | 8/2004 | Case et al. | |
| 2004/0199177 A1 | 10/2004 | Kim | |
| 2004/0215339 A1 | 10/2004 | Drasler et al. | |
| 2004/0254636 A1 | 12/2004 | Flagle | |
| 2004/0260390 A1 | 12/2004 | Sarac | |
| 2005/0085903 A1 | 4/2005 | Lau | |
| 2005/0203605 A1 | 9/2005 | Dolan | |
| 2005/0245894 A1 | 11/2005 | Zadno-Azizi | |
| 2006/0020327 A1 | 1/2006 | Lashinski et al. | |
| 2006/0034883 A1 | 2/2006 | Dang et al. | |
| 2006/0089708 A1 | 4/2006 | Osse et al. | |
| 2006/0111773 A1 | 5/2006 | Rittgers | |
| 2006/0178729 A1 | 8/2006 | Thielen et al. | |
| 2007/0027528 A1 | 2/2007 | Agnew | |
| 2007/0027535 A1 | 2/2007 | Purdy, Jr. et al. | |
| 2007/0100432 A1 | 5/2007 | Case et al. | |
| 2007/0129788 A1 | 6/2007 | Drasler et al. | |
| 2007/0142897 A1 | 6/2007 | Consigny et al. | |
| 2007/0255394 A1 | 11/2007 | Ryan | |
| 2008/0125853 A1 | 5/2008 | Bailey et al. | |
| 2008/0177373 A1 | 7/2008 | Huang et al. | |
| 2008/0178459 A1 | 7/2008 | Barr et al. | |
| 2008/0234728 A1 | 9/2008 | Starksen et al. | |
| 2008/0269877 A1 | 10/2008 | Jenson et al. | |
| 2008/0288055 A1 | 11/2008 | Paul, Jr. | |
| 2008/0312735 A1 | 12/2008 | Thorpe et al. | |
| 2009/0084844 A1 | 4/2009 | Jung et al. | |
| 2009/0105810 A1 | 4/2009 | Jaffe | |
| 2009/0164003 A1 | 6/2009 | Kheradvar | |
| 2009/0171267 A1 | 7/2009 | Bonnette et al. | |
| 2009/0177270 A1 | 7/2009 | Agnew et al. | |
| 2009/0248139 A1 * | 10/2009 | Pellegrini | A61F 2/91 623/1.15 |
| 2009/0264991 A1 | 10/2009 | Paul, Jr. et al. | |
| 2009/0324710 A1 | 12/2009 | Glidden et al. | |
| 2010/0057115 A1 | 3/2010 | Rao et al. | |
| 2010/0131055 A1 | 5/2010 | Case et al. | |
| 2010/0152682 A1 | 6/2010 | Mauch et al. | |
| 2010/0152843 A1 | 6/2010 | Mauch et al. | |
| 2010/0241047 A1 | 9/2010 | Yacoubian et al. | |
| 2010/0331965 A1 | 12/2010 | Dugas et al. | |
| 2011/0009749 A1 | 1/2011 | Zamboni | |
| 2011/0021986 A1 | 1/2011 | Zamboni | |
| 2011/0060405 A1 | 3/2011 | Richardson et al. | |
| 2011/0282369 A1 * | 11/2011 | Krolik | A61B 17/320725 606/198 |
| 2012/0046733 A1 | 2/2012 | von Oepen et al. | |
| 2012/0046739 A1 | 2/2012 | von Oepen et al. | |
| 2012/0191112 A1 | 7/2012 | Zamboni | |
| 2012/0191727 A1 | 7/2012 | Zamboni | |
| 2013/0023764 A1 | 1/2013 | Brown et al. | |
| 2013/0211489 A1 | 8/2013 | Makower et al. | |
| 2014/0039484 A1 | 2/2014 | Leung | |
| 2015/0164642 A1 | 6/2015 | Khosravi et al. | |

FOREIGN PATENT DOCUMENTS

| | | |
|---|---|---|
| WO | WO 2005/023153 | 3/2005 |
| WO | WO 2008/140466 | 11/2008 |
| WO | WO 2009/088957 | 7/2009 |
| WO | WO 2011/100263 | 8/2011 |

OTHER PUBLICATIONS

Dake, *CCSVI: What We Need to Know Now and in the Future*, Endovascular Today, Jul. 1, 2011.

Jeffrey, *CCSVI in Focus at ECTRIMS: New Data But Still Little Clarity*, Nov. 12, 2010 (Göteborg, Sweden).

Ludyga et al., *Endovascular treatment for chronic cerebrospinal venous insufficiency: is the procedure safe?*, Phlebology 2010, PHLEB-10-053, pp. 1-10.

Mandato, *Retrospective study finds angioplasty for internal Jugular and azygous veins safe at 30 days*, News and updates, May 2011, International News, BIBA Publishing.

(56) References Cited

OTHER PUBLICATIONS

Mussa et al., *Iliac Vein Stenting for Chronic Venous Insufficiency*, Texas Heart Institute Journal, 2007, vol. 34, No. 1, pp. 60-66.

Saposnik et al., *Diagnosis and Management of Cerebral Venous Thrombosis: A Statement for Healthcare Professions From the American Heart Association/American Stroke Association*, stroke.ahajournals.org, Feb. 4, 2011, Stroke Apr. 2011.

Siskin et al., *Chronic Cerebrospinal Venous Insufficiency in Multiple Sclerosis Patients*, Endovascular Today, Jul. 2011.

Zamboni et al., *Chronic Cerebrospinal Venous Insufficiency in Patients with Multiple Sclerosis*, J. Neurol Neurosurg Psychiatry, Apr. 2009, vol. 80, No. 4, pp. 392-399.

Zamboni, *A prospective open-label study of endovascular treatment of chronic cerebrospinal venous insufficiency*, Journal of Vascular Surgery, Dec. 2009, vol. 50, No. 6, pp. 1348-1358.e3.

\* cited by examiner

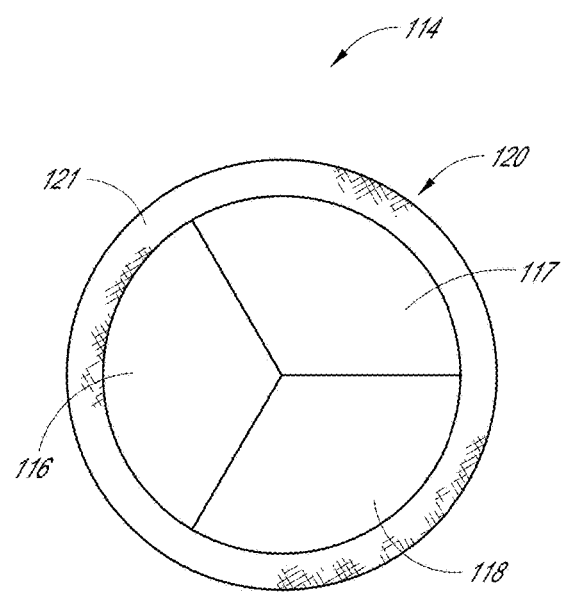 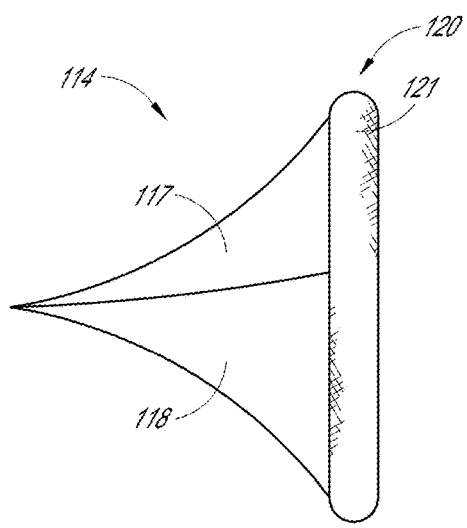
*FIG. 15A*  *FIG. 15B*
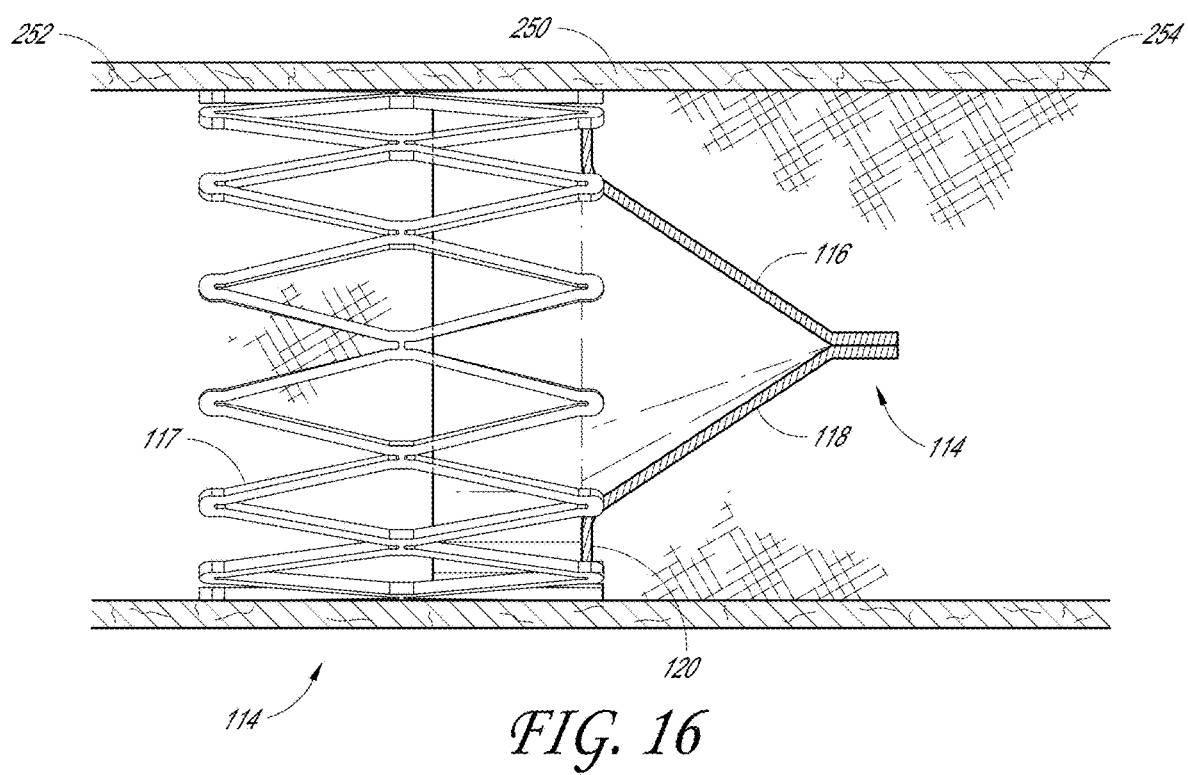
*FIG. 16*

METHODS AND APPARATUS FOR TREATING NEUROVASCULAR VENOUS OUTFLOW OBSTRUCTION

CROSS-REFERENCE TO RELATED APPLICATIONS

This application is a continuation of U.S. patent application Ser. No. 15/589,032, filed on May 8, 2017, which is a continuation of U.S. patent application Ser. No. 14/550,748, filed on Nov. 21, 2014 (now issued as U.S. Pat. No. 9,675,457), which is a continuation of U.S. patent application Ser. No. 13/191,296, filed on Jul. 26, 2011 (now abandoned), which claims the priority benefit of U.S. Provisional Application No. 61/400,383, filed Jul. 27, 2010. The entireties of each of the foregoing applications is hereby incorporated by reference herein.

BACKGROUND OF THE INVENTION

The present invention relates to methods and devices for treating neurovascular venous outflow obstructions, such as to relieve the symptoms of multiple sclerosis or other neurological conditions.

Multiple Sclerosis (MS) is a debilitating disease for which modern medicine has few answers. Questions remain regarding the etiology, the disease process, and possible treatments. Since Jean Martin Charcot first described the clinical and pathological features of MS in 1868 it has perplexed physicians and scientists alike. For years the disease was described clinically, but with the advent of more sophisticated tools such as magnetic resonance imaging (MRI), the disease process was linked to plaques—or inflammatory lesions—in the white matter of the central nervous system. These lesions were characterized by a breakdown of the myelin sheath that surrounds the central axon of a nerve cell. The first clinical signs are thought to manifest years after the pathology begins in the brain. There is also increasing evidence that the pathology is much more widespread than the finite number of lesions seen on MRI. In addition, serial MRI studies have shown that the disease process is ongoing even when clinical symptoms seem to have subsided.

The pathophysiology of the disease process has been described and is believed to involve an autoimmune component; however, the precise underlying etiology remains a mystery. MS has been associated with past Epstein Barr Virus (EBV) exposure, smoking, geography, and it is believed to have some genetic component. MS affects more than 350,000 people in the United States. Estimates of the prevalence of the disease are approximately 90 cases per 100,000 people.

The symptoms of an MS attack or flare can include: paresthesias, limb weakness, paralysis, double vision, loss of vision, incontinence, and cognitive decline. There are three main clinical courses of MS: Relapsing Remitting (RR); Secondary Progressive (SP); and Primary Progressive (PP). RR is characterized by acute exacerbations of the disease followed by complete remission of the symptoms with nearly complete recovery. Some patients with the RR course of the disease will not completely return to their baseline level of function. SP is characterized by progressive deterioration of neurologic function. Most patients with the RR course of the disease will eventually develop SP after several years with RR. PP is characterized by a progressive clinical course from the onset of the disease.

In terms of the pathophysiology, MS involves the breakdown of the myelin sheath that surrounds the central axon of a nerve. There also appears to be widespread axonal damage. In addition, though the disease had often been considered a white matter disease, there is now some evidence of pathology in the grey matter of the brain as well. Though the genetic aspect of MS has been studied there has been no direct genetic link identified. Despite the complicated set of immunological changes that affect the myelin and axons having been studied extensively for years. In addition, there is epidemiological evidence that points to some variable incidence of MS in different parts of the world. And yet, despite all this extensive attention and study, a cure or even an effective treatment for MS remains out of reach.

The best medicine can provide at this point for a patient is to delay the progression of the disease. And eventually even these patients will only have their symptoms managed to maximize their quality of life as the disease inevitably progresses. There is a focus in these early treatments on the few mechanisms thought to be important in the progression of the disease. Anti-inflammatory therapy has been used for acute attacks of the disease, which has no more than short-term benefit to shorten the duration of the attack. Immunosuppressive therapies have been attempted but have provided little benefit and led to substantial side effects. As understanding of the specific immunological mechanisms involved in the disease process improve there are more targeted agents being studied.

For almost four decades neurologists have been able to modify the acute attacks of the disease. Since the 1990's the agents addressing the number and severity of attacks of MS have improved, and have reduced the activity seen on MRI. However, there remains no long-term data that convincingly demonstrates a reduction in the rate of eventual progression of the disease. The various therapies used for MS have been applied by trial and error and changed as the theory of the disease changed. There is now some new evidence that venous blood flow from the brain may play a role in MS.

The venous circulatory system flowing from the brain is complicated. Blood is drained from the brain by back propulsion of the residual arterial pressure (i.e., negative venous pressure), and antegrade postural and respiratory mechanisms. The internal jugular vein (IJV) collects the blood from the brain, face, and neck. The IJV is directly continuous with the sigmoid sinus in the jugular foramen at the base of the skull. At the origin of the IJV, the vein is somewhat dilated—this dilatation is called the superior bulb. It runs down the side of the neck in a vertical direction, lying at first lateral to the internal carotid artery, and then lateral to the common carotid. At the root of the neck the IJV unites with the subclavian vein (SV) to form the innominate vein. A little above its termination is a second dilatation called the inferior bulb. At the root of the neck, the right IJV is farther from the common carotid, and crosses the first part of the subclavian artery, while the left IJV usually overlaps the common carotid artery. The left IJV is generally smaller than the right, and each contains a pair of valves, which are about 2.5 cm above the termination of the vessel. The external jugular (EJV) vein receives the greater part of the blood from the exterior of the cranium and the deep parts of the face, being formed by the junction of the posterior division of the retromandibular vein with the posterior vein. The EJV has two pairs of valves, the lower pair is at the intersection with the SV, and the upper in most people is about 4 cm above the clavicle. The portion between the two valves is often dilated and is called the sinus. These valves do not prevent the regurgitation of blood or the passage of blood from below upward. Supine posture favors cerebral venous outflow through the IJV veins. In the upright position, blood is redirected through the vertebral veins and the azygous vein (AZ) which becomes the predominant pathway.

There are valves in the IJV in more than 90% of patients. These valves are frequently located in the distal portion of the IJV. Sonography demonstrates bilateral valves in 60% of patients, with the majority of unilateral valves are right sided. Doppler ultrasound (US) of the IJV has demonstrated symmetrical biphasic blood flow in 57% of 148 patients, continuous flow in 29%, and monophasic flow in 13%. Scientists have hypothesized blood flow velocity normal when it is less than 1 m/s and varies with both respiration and heart rate. Others have reported an average right-plus-left jugular vein flow of 740±209 ml/min. Flow was 8.7% lower in female than in male subjects, but normalization of flow to 100 g brain tissue failed to reveal any significant sex difference. Normal Doppler US waveforms are characterized by two physiological variations: 1) cardiac pulsatility, due to the retrograde pressure waves of right atrial contraction, is synchronized to the pulse rate and frequently results in a biphasic signal; 2) superimposed variations related to the respiratory cycle, with an increase on inspiration and a decrease on expiration.

IJV valve incompetence has been documented for many years, and is hypothesized to be associated with various disease process including respiratory brain syndrome and cough headaches. The IJV valve is situated just above the termination of the IJV and is the only valve between the heart and the brain. If the IJV valve is damaged or becomes incompetent, increase in intrapleural pressure could result in raised intracranial pressure. Additionally, the jugular venous pulse is used clinically to estimate right atrial pressure. A high prevalence of IJV valve insufficiency appears to be present in patients with clinical diagnosis of transient global amnesia (TGA)—suggesting that venous congestion in areas of the brain associated with memory may partially explain episodes of benign TGA. IJV valve insufficiency has been found to be present in at least 1 side in almost 80% of patients with TGA, compared with only 25% of control subjects. There was also a trend toward a predominance of right-sided IJV valve insufficiency. Studies have shown valvular insufficiency in nearly 80% of subjects with TGA compared to 25% of subjects with no history of TGA.

Ever since Jean Martin Charcot first described MS, the plaques were known to be venocentric. Since then magnetic resonance venographs (MRVs) and postmortem studies have shown a central vein oriented along the long axis of the inflammatory lesion. In addition, the brains and spinal cords of patients with MS contain abnormally high levels of redoxactive metals, particularly iron, as documented by advanced MRI studies. Histologic studies have shown disposition of iron stores in CNS venous walls in patients with MS. In the 80's it was hypothesized that MS might be related to cardiorespiratory blood "backjets" as the basis for the Dawson's Fingers, which are lesions seen around the CNS veins near the ventricle in MS patients.

A condition called Chronic Cerebrospinal Venous Insufficiency (CCSVI) has been hypothesized to be associated with MS. Researchers have described CCSVI as a condition with multiple stenoses of the principal pathways of the extracranial venous drainage, such as the IJV and Azygous vein (AV). A study from 2009 looking at 65 MS patients (35 with RR; 20 with SP; and 10 with PP) and 265 controls (60 healthy-age and gender matched; 82 healthy but older than study group; 45 with other neurological disease; 48 with other disease scheduled for venography) examined the flow in the azygous and jugular venous system. Zamboni et al., *Chronic Cerebrospinal Venous Insufficiency in Patients with Multiple Sclerosis*, 80 J. NEUROLOGY NEUROSURGERY & PSYCHIATRY 392 (2009). The study focused on detection of five parameters, which are said to be absent in normal subjects: 1) reflux in the IJV and/or vertebral veins (VVs) in sitting and supine posture; 2) reflux in the deep cerebral veins (DCVs); 3) high-resolution B-mode evidence of IJV stenoses; 4) flow not Doppler-detectable in the IJV and/or VVs; and 5) reverted postural control of the main cerebral venous outflow pathways. All patients with at least 2 of these criteria were reported to have "multiple significant extra-cranial stenoses" by venography. Of the patients with these extra-cranial stenoses, 91% had IJV stenoses and 86% had AV stenosis. Of the five criteria above the study reported a statistically significant difference between patients with MS and those without in each of the criteria to a P<0.001 level of significance.

Notwithstanding the foregoing, there remains a need for methods and devices for treating neurovascular venous outflow obstructions, such as to relieve the symptoms of Multiple Sclerosis or other neurological conditions or disease.

SUMMARY OF THE INVENTION

There is provided in accordance with the present invention methods and devices for treating cerebrospinal venous insufficiency, which treatment may reduce or eliminate certain symptoms of multiple sclerosis or other neurological conditions. In accordance with the methods of the present invention, a patient is identified having at least a partial obstruction at a site in the venous outflow track from the brain. Patency is restored by at least partially removing the obstruction, and a valve is implanted in fluid communication with the site, to permit venous outflow and reduce retrograde pressure. The valve may be implanted at the site, or in upstream or downstream fluid communication with the site.

The removing the obstruction step may comprise inflating a dilatation balloon at the site. The dilatation balloon may additionally carry an implant at the time of the inflating step to remove the obstruction. Alternatively, following removal of the obstruction, a deployment balloon may be positioned at the site carrying an implant for balloon deployment. The deployment balloon may be carried by a catheter, which is introduced into the vasculature at an access point spaced apart from the site.

The removing the obstruction step may comprise surgically removing a section of vein. The implanting step may comprise surgically attaching a valve, or a graft containing a valve, at the site.

The method may comprise attaching a first end of a graft at a first anastomosis to a vein and attaching a second end of the graft at a second anastomosis to a vein. The first anastomosis may be to the right internal jugular, the left internal jugular or the azygos vein. The second anastomosis may be to the right internal jugular, the left internal jugular, the right innominate, the left innominate the azygos or the superior vena cava.

Alternatively, a valve may be implanted in one or more of the left internal jugular, the right internal jugular, the azygos and the superior vena cava.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 15A is a schematic plan view of a three-leaflet valve, having a fabric covered annulus for surgical attachment to a vein.

FIG. 15B is a side elevational schematic view of the valve of FIG. 15A.

FIG. 16 is a side elevational schematic view of a valved graft for surgical implantation.

DETAILED DESCRIPTION OF THE PREFERRED EMBODIMENT

Figure 1:
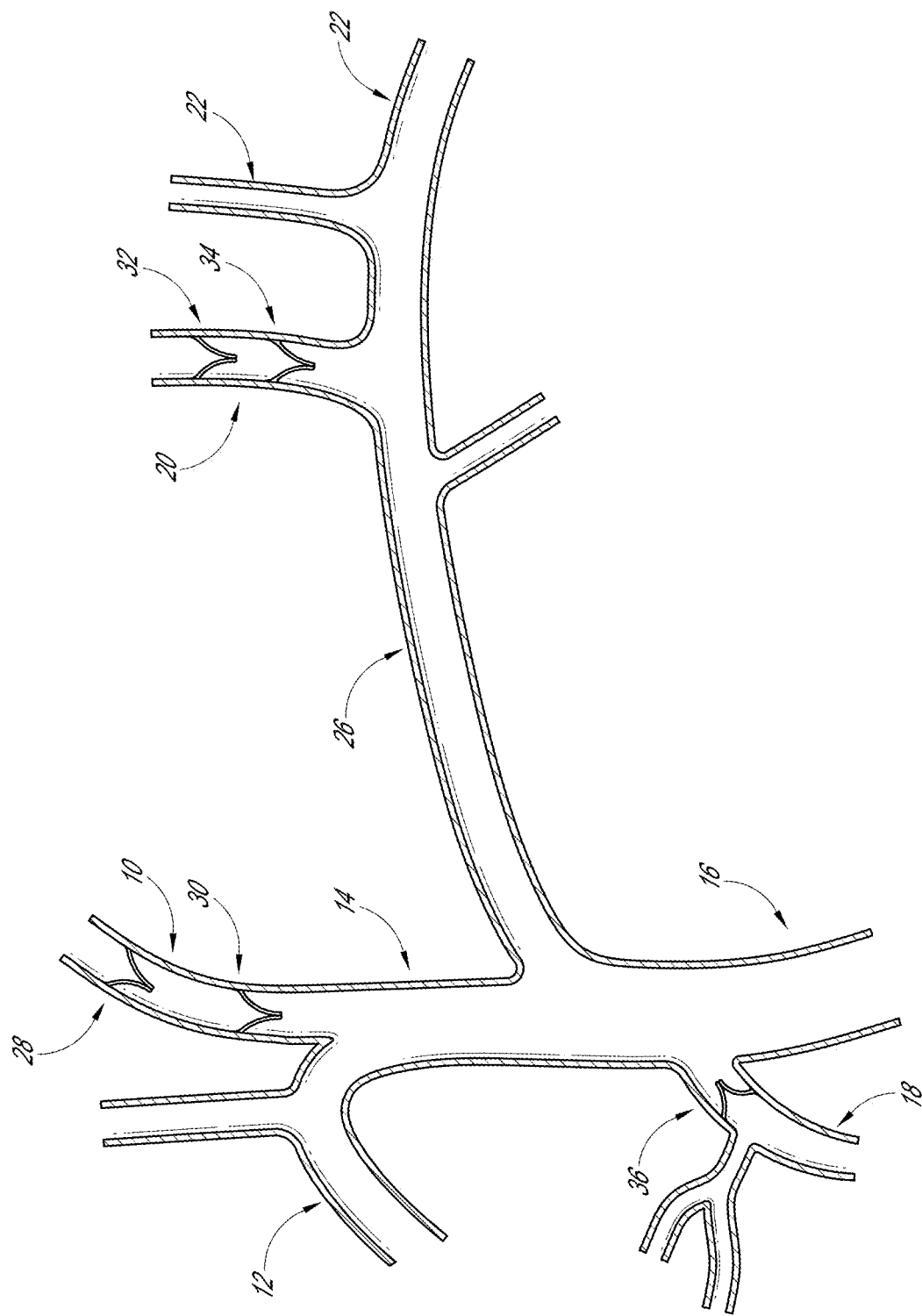
FIG. 1 is a schematic view of the venous outflow vasculature leading from the brain.

Referring to FIG. 1, there is illustrated a simplified schematic of the venous outflow vasculature leading from the brain. As illustrated therein, venous flow from the vein is conducted via the right internal jugular vein 10 which merges with the subclavian vein 12 to form the right innominate 14, leading to the superior vena cava 16. The azygos vein 18 also leads to the superior vena cava 16.

Venous flow through the left internal jugular 20 and external jugular 22 merge with the subclavian vein 24, and lead via the left innominate 26 to the superior vena cava 16.

The extracranial venous vasculature described above is typically also characterized by the presence of a number of valves. Although patient-to-patient variation is observed, a typical patient may have a first valve 28 and a second valve 30 within the right internal jugular 10. The left internal jugular 20 may also be provided with a first valve 32 and a second valve 34. In addition, the azygos vein 18 is often found with at least one valve 36.

In a healthy patient, the valves function to permit outflow from the cerebral vasculature, while inhibiting retrograde flow and/or pressure throughout the cardiac cycle.

Anomalies in the venous outflow track from the brain have been associated with a variety of neurological conditions. For example, malformed or deformed valves can lead to regurgitant flow. Venous stenosis, which may result from either the formation of thrombus or plaque, or from extreme twisting or bending of the vein, can produce resistance to normal venous drainage. Stenotic legions in the venous vasculature are often observed in the vicinity of or involving one or more valves, or may be spaced apart from the valves.

In accordance with the present invention, one or more therapeutic procedures which may involve an implant are accomplished on the extracranial venous vasculature, to alleviate an abnormality in venous blood flow. As is discussed in greater detail below, the procedure may be accomplished either via a direct surgical incision, or transvascularly using one or more catheters introduced into the venous system at a remote site. The procedure may involve restoring patency to the venous lumen, such as by balloon dilatation or other recanalization technique. The procedure may additionally involve deployment of a permanent or temporary implant, such as a tubular scaffold to inhibit restenosis of the venous lumen. One or more valves may also be deployed, and oriented to permit venous outflow but resist regurgitant pressure and/or flow. Various aspects of the invention will be described in additional detail below.

Figure 2:
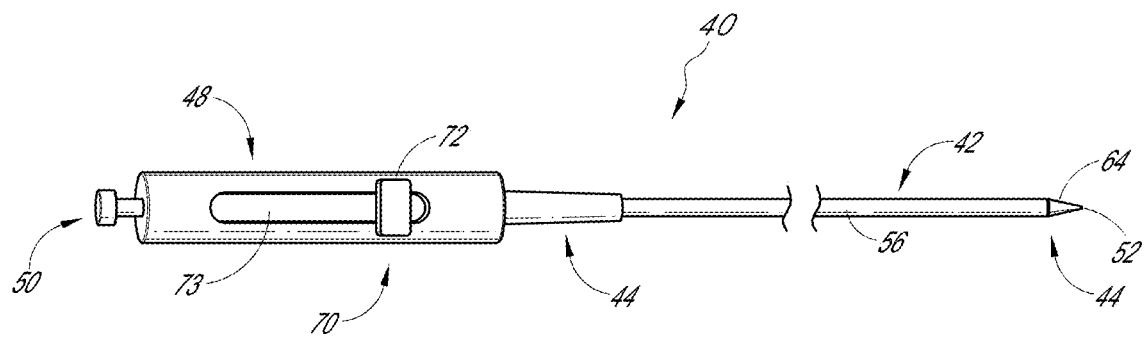
FIG. 2 is a schematic side elevational view of a deployment catheter in accordance with one aspect of the present invention.

Referring to FIG. 2, there is disclosed a catheter 40 in accordance with one aspect of the present invention. Although primarily described in the context of a deployment catheter having a retractable outer sheath to release a self expanding implant, catheters of the present invention can readily be modified to incorporate a variety of additional structures and functionalities, such as permanent or removable column strength enhancing mandrels, two or more lumen such as to permit drug or irrigant infusion or radiation delivery or to supply inflation media to an inflatable balloon, or to permit aspiration or other removal of thrombus, or combinations of these features, as will be readily apparent to one of skill in the art in view of the disclosure herein. In addition, the present invention will be described primarily in the context of restoring flow in the outflow vasculature from the brain, although the devices disclosed herein may be introduced into other veins, arteries or hollow structures in the body.

The catheter 40 generally comprises an elongate tubular body 42 extending between a proximal end 44 and a distal functional end 46. The length of the tubular body 42 depends upon the desired application. For example, lengths in the area of from about 120 cm to about 140 cm or more are typical to reach the jugular veins via femoral access. A different catheter shaft length may be appropriate depending upon the vascular access site, as will be understood in the art.

The proximal end 44 of catheter 40 is additionally provided with a handle 48 having one or more access ports as is known in the art. Generally, handle 48 is provided with a guidewire port 50 in an over-the-wire construction, and optionally an aspiration or infusion port (not illustrated). The guidewire port 50 may comprise a standard luer connector, and is in communication with a distal guidewire access port 52 by way of an elongate guidewire lumen 54. Alternatively, aspiration or infusion may be accomplished through the guidewire lumen in an OTW configuration if the guidewire is proximally retracted following placement of the catheter 40.

A rapid exchange configuration may be provided, by eliminating the proximal luer connector at the proximal guidewire port 50, and positioning the proximal guidewire port 50 along the side wall of the tubular body 42. Generally, the proximal guidewire access port 50 in a rapid exchange configuration will be positional within about 20 cm, and, in some embodiments, within about 10 cm from the distal guidewire port 52 as is understood in the art. Additional access ports may be provided as needed, depending upon the desired functional capabilities of the catheter. Handle 48 may be injection molded from any of a variety of medical grade plastics, or formed in accordance with other techniques known in the art.

Figure 3:
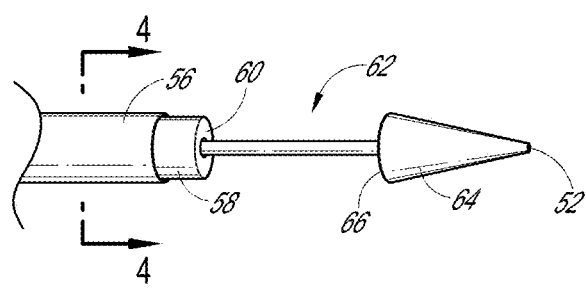
FIG. 3 is a detailed view of the distal end of the catheter illustrated in FIG. 2, with an outer sheath in a proximal, retracted configuration.

Referring to FIG. 3, the catheter 40 comprises an axially moveable outer sleeve 56 which is shown in a proximally retracted orientation. Sleeve 56 is axially moveably carried by an elongate core 58, which steps down in diameter at a distally facing shoulder 60 to provide an annular recess 62 for releasably receiving an implant. The distal end of the core 58 is provided with an atraumatic tip 64, to facilitate in navigation and minimize trauma to the vessel wall. Tip 64 extends from the distal guidewire port 52 to a proximal end 66 configured to provide a smooth exterior surface when the outer sleeve 56 is in a distal position to enclose and restrain an implant within the chamber formed by annular recess 62.

Figure 4:
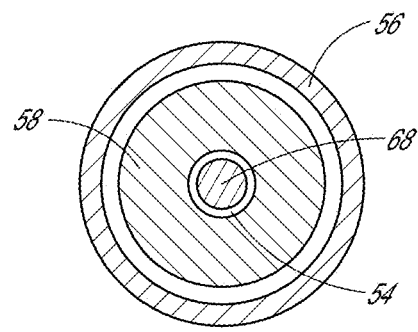
FIG. 4 is a cross-sectional view taken along the lines 4-4 in FIG. 3.

The cross-sectional view of FIG. 4 illustrates the outer sleeve 56 axially moveably carried by the flexible core 58, and shows a guidewire 68 positioned within the central guidewire lumen 54.

Referring back to FIG. 2, handle 48 is additionally provided with a control 70, for controlling the axial position of the outer sleeve 56 relative to core 58. Control 70 may take any of a variety of forms depending upon the desired physician interface. In the illustrated embodiment, control comprises an axially moveable slider switch 72 which is movable along an axial slot 73. Slider switch 72 is mechanically linked to the outer sleeve 56 such that proximal retraction of the slider switch 72 produces a proximal movement of the sleeve. This exposes the annular recess 62 and allows deployment of a self-expandable implant restrained therein.

Any of a variety of controls 70 may be utilized, including switches, levers, rotatable knobs, pull/push wires, and others which will be apparent to those of skill in the art in view of the disclosure herein.

Avoiding a tight fit between the guidewire 68 and inside diameter of guidewire lumen 54 enhances the slideability of the catheter over the guidewire. In ultra small diameter catheter designs, it may be desirable to coat the outside surface of the guidewire 68 and/or the inside surface of the wall defining lumen 54 with a lubricous coating to minimize friction as the catheter 40 is axially moved with respect to the guidewire 68. A variety of coatings may be utilized, such as Paralene, Teflon, silicone rubber, polyimide-polytetrafluoroethylene composite materials or others known in the art and suitable depending upon the material of the guidewire or inner tubular wall of lumen 54.

In general, the inside diameter of guidewire lumen 54 will be at least about 0.003 inches or greater larger than the outside diameter of the intended guidewire. Guidewires having diameters in the range of from about 0.009 inches to about 0.016 inches are presently contemplated.

Catheters of the present invention which are adapted for intracranial applications generally have a total length in the range of from 60 cm to 250 cm, usually from about 135 cm to about 175 cm. The length of the proximal segment 33 will typically be from 20 cm to 220 cm, more typically from 100 cm to about 120 cm.

The catheters of the present invention may be constructed from any of a variety of known biologically compatible polymeric resins having suitable characteristics when formed typically by extrusion into the tubular catheter body segments. Exemplary materials include a variety of medical grade polyvinyl chloride, polyethers, polyamides, polyethylenes, polyurethanes, copolymers thereof, and the like. Suitable species include PEBAX, PEEK, and others known in the angioplasty arts. In certain embodiments, the distal tip 64 may be formed from more elastic materials, such as latex rubber, silicone rubber, and blends thereof.

The catheter body 42 may further comprise other components, such as radiopaque fillers; colorants; reinforcing materials; reinforcement layers, such as braids and helical reinforcement elements; or the like. In particular, a proximal zone on body 42 may be reinforced in order to enhance its column strength and torqueability while preferably limiting its wall thickness and outside diameter.

Radiopaque markers may be provided at least at the proximal and/or distal ends of the annular recess 62. The implant may comprise a radiopaque material or be provided with markers. Other radiopaque markers may be provided elsewhere, such as on the distal end of the movable sleeve 56. One radiopaque marker comprises a metal band which is embedded within the wall of the sleeve 56 or core 58. Suitable marker bands can be produced from a variety of materials, including platinum, gold, and tungsten/rhenium alloy.

The tubular body 42 may be produced in accordance with any of a variety of known techniques for manufacturing interventional catheter bodies, such as by extrusion of appropriate biocompatible polymeric materials. Alternatively, at least a proximal portion or all of the length of tubular body 16 may comprise a polymeric or metal spring coil, solid walled hypodermic needle tubing, or braided reinforced wall, as is known in the microcatheter arts.

In many applications, the tubular body 42 is provided with an approximately circular cross-sectional configuration having an external diameter within the range of from about 0.025 inches to about 0.065 inches. Alternatively, a generally oval or triangular cross-sectional configuration can also be used, as well as other noncircular configurations, depending upon the method of manufacture, number and arrangement of internal lumens and the intended use.

In a catheter intended for peripheral vascular applications, the body 42 may have an outside diameter within the range of from about 0.039 inches to about 0.065 inches. In coronary vascular applications, the body 42 may have an outside diameter within the range of from about 0.025 inches to about 0.045 inches. Catheters configured to access the external jugular vein 22 will typically have an outside diameter of no more than about 0.045 inches, and as low as about 0.028 inches or about 0.025 inches or about 0.022 inches or lower.

Diameters outside of the preferred ranges may also be used, provided that the functional consequences of the diameter are acceptable for the intended purpose of the catheter. For example, the lower limit of the diameter for any portion of tubular body 42 in a given application will be a function of the number of fluid or other functional lumen contained in the catheter, together with the collapsed diameter of the implant.

Tubular body 42 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation, to assist in steering. The tubular body 42, may be provided with any of a variety of torque and/or column strength enhancing structures. For example, axially extending stiffening wires, spiral wrapped support layers, braided or woven reinforcement filaments may be built into or layered on the tubular body 16. See, for example, U.S. Pat. No. 5,891,114 to Chien, et al., the disclosure of which is incorporated in its entirety herein by reference.

Alternatively, any of a variety of the implants disclosed herein can be configured for deployment from a balloon catheter. In a most basic embodiment, a balloon expandable stent is provided with a valve and carried in a collapsed configuration over a deflated balloon to the deployment site. The balloon is inflated at the deployment site to expand the stent, leaving the stent and valve construct at the deployment site following deflation and proximal retraction of the balloon catheter. Many of the dimensions and considerations previously discussed in connection with self-expandable implant deployment systems will also guide the design of suitable balloon catheter deployment systems. Balloon catheters intended for deployment of an implant in the azygos vein may have an inflated balloon diameter within the range of about 6 mm to about 8 mm, and an inflated diameter within the range of about 8 mm to 16 mm for balloons intended to deploy an implant in the jugular vein.

Certain stenoses in the extracranial venous vasculature require a relatively high inflation pressure in order to recanalize the lumen. Inflation pressures of at least about 18 atmospheres or 20 atmospheres or more are often desirable. As a consequence, deployment of a self-expanding implant preferably will be preceded by a balloon dilatation. The valves associated with balloon expandable implants, particularly if a tissue valve is utilized, may or may not tolerate the compression resulting from high inflation pressures. Thus, depending upon the valve design, either a pre-implantation balloon dilatation may be preferred, or the dilatation can be accomplished simultaneously with expansion of the implant at the deployment site.

Resistant stenoses may alternatively be dilated using a cutting balloon. Cutting balloons are known in the percutaneous transluminal coronary angioplasty arts, and include one or more axially elongate incising elements mounted on the exterior of the inflatable balloon. One example of a cutting balloon may be seen in U.S. Pat. No. 7,799,043 to O'Brien et al. (Boston Scientific) the disclosure of which is hereby incorporated in its entirety herein by reference.

As a further alternative, the implant may be a two or more part construct which is assembled in situ at the deployment site. For example, a support structure such as a stent can be carried by a balloon to the deployment site, and expanded under high pressure to generate sufficient radial force to dilate both the stent and the lesion utilizing a first procedure catheter. A second procedure catheter may thereafter be introduced and positioned within the support structure, to deploy the valve. The valve deployment may either be accomplished by a balloon catheter, which may have a lower inflation pressure than the first procedure catheter, or in a self-expanding mode. The valve is coupled to the support structure, to produce the final construct.

Certain exemplary valve and support structure constructs will be described below. The present invention contemplates the use of any of the valve structures described below with any of the support structures described below, and not merely the specific examples given. In general, the implant can take any of variety of forms including a tubular scaffold without a valve, or a tubular scaffold with a valve on the same device. Alternatively, the tubular scaffold and the valve may be separately implanted and connected or associated in situ. Any of the valves disclosed herein may be alternatively be configured for anchoring to the vessel wall or within the vessel using a structure other than a tubular scaffold. As used herein, terms such as scaffold or support structure may include a form of a stent, but also include intravascular support structures which might not be considered a stent. The support structures can be balloon expandable, or self-expandable, or not expandable at all, such as in the case of certain hooks or barbs, depending upon the desired configuration.

Figure 5A:
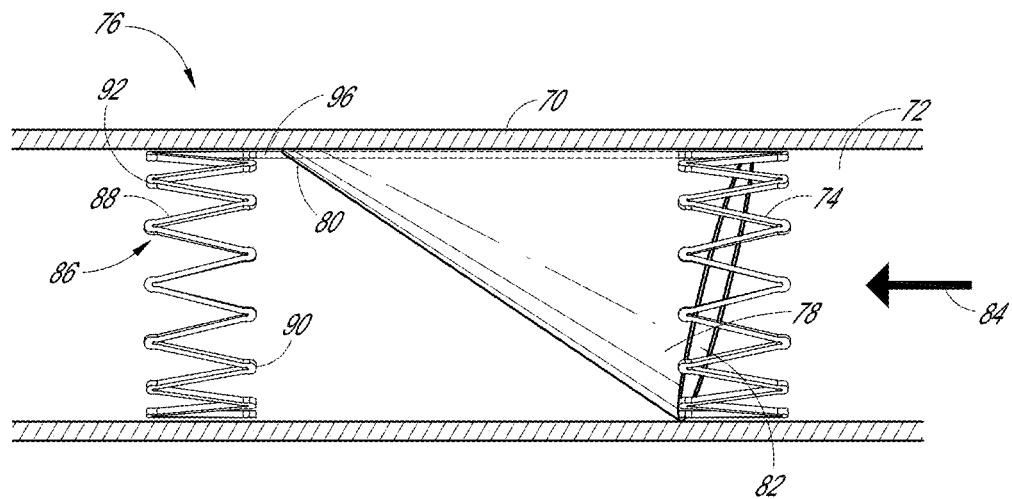
FIG. 5A is a side elevational view of a flow directed valve positioned within a vein, in a closed configuration.
Figure 5B:
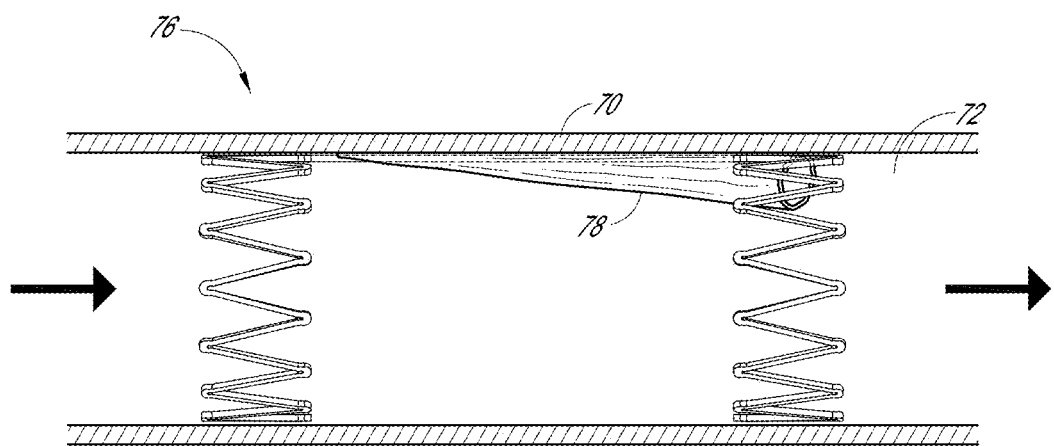
FIG. 5B is a side elevational view as in FIG. 5A, with the valve in an open position.

Referring to FIGS. 5A and 5B, there is illustrated one exemplary valve in accordance with the present invention. As illustrated therein, the tubular wall 70 of the vein defines a blood flow lumen 72. An implant 74 is positioned within the lumen 72. The implant comprises a support structure 76 which supports at least one occluder 78.

In the illustrated embodiment, the occluder is in the form of a collapsible cone or wind sock extending from an apex 80 at an upstream end to a downstream opening 82 having a fully opened diameter at least as great as the inside diameter of the lumen. The occluder 78 is secured at apex 80 and at one or more points along its length on a first, fixation side of the occluder to the support structure 76. A second, opposing dynamic side of the implant 74 is moveable between a radially expanded (occlusive) configuration as illustrated in FIG. 5A and a radially compressed configuration as illustrated in FIG. 5B.

As implanted in a vessel, retrograde flow 84 has a tendency to enter the open end of the occluder in a manner like a wind sock and advance the dynamic side across the lumen to occlude further retrograde flow. Referring to FIG. 5B, antegrade flow (e.g. towards the heart) has the effect of collapsing the occluder 78 by forcing the dynamic side against the wall of the lumen and permitting forward flow.

Although illustrated as having only a single occluder 78, two or three or four or more inflatable and collapsible occluder elements may cooperate with each other to achieve the same functionality, in which the valve is either opened or closed in response to the direction of blood flow.

The occluder 78 may comprise any of a variety of materials, preferably in the form of a thin blood impermeable membrane. Preferably, the membrane is highly compliant and responsive to subtle changes in blood flow. The thickness of the membrane can be optimized by those of skill in the art in view of the composition of the membrane. Presently contemplated ePTFE membranes will typically have a thickness of no more than about 0.01 inches and, in some embodiments, no more than about 0.005 inches or 0.001 inches or less. Ultrathin membranes of any of a variety of polymers utilized in the catheter arts may also be used, such as nylon, polyethylene terephthalate, PEEK, various densities of polyethylene and others known in the art. Alternatively, ultrathin metal mesh membrane or porous metal membranes may be utilized, provided that they demonstrate the desired physical properties.

Preferably, the material of the membrane as well as the support structure will be antithrombogenic or at least resist thrombus formation either inherently, or through the provision of an antithrombotic coating.

In the ultrathin membrane embodiments, one or two or more axially extending struts may desirable be incorporated within or attached to the occluder 78, to improve the structural integrity of the membrane in the environment of high velocity blood flow. Depending upon the desired performance, the membrane may either be completely impermeable to blood flow, or may be provided with a level of porosity that permits a small amount of retrograde blood flow. Pore sizes of no more than about 100µ and in some embodiments no more than about 50µ or 20µ may be used.

The support structure 76 may comprise any of a variety of balloon expandable or self-expandable stents, or other support structure that is sufficient to retain the occluder 78 at the desired deployment site and resist migration under the force of blood flow. Thus, for example, the apex 80 may be secured directly to the vessel wall, using any of a variety of attachment techniques such as clips, sutures, staples, or other barb structures which extend into and optionally through the wall 70.

In the illustrated embodiment, the support structure 76 comprises at least one self-expanding tubular support in the form of a stent 86. The stent comprises a plurality of struts 88 extending in a zig-zag fashion having a plurality of alternating proximal apexes 90 and distal apexes 92, a structure some times referred to as a "Z" stent. The struts 88 may comprise any of a variety of materials having suitable properties, such as Nitinol, stainless steel, Elgiloy or others known in the art.

In the illustrated embodiment, a first tubular support 86 is spaced axially apart from a second tubular support 94 and connected by an axially extending strut 96. The axially extending strut 96 serves to both maintain the spatial relationship of the first and second tubular supports, as well as provide an attachment structure for the fixation side of the conical occluder. The occluder may be attached to the support structure at the point of manufacture, and introduced into the vessel as a single unit. Alternatively, the support structure may be deployed in a first step, and the occluder carried into position and attached to the support structure in situ in a second step.

Figure 6A:
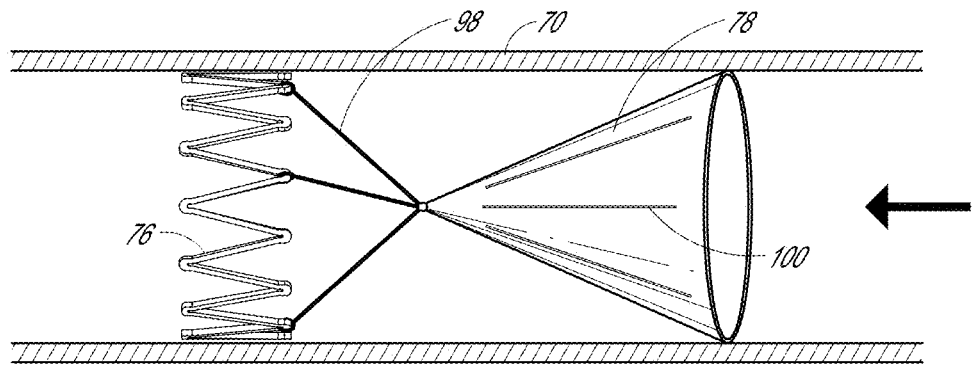
FIG. 6A is a side elevational view of an alternate valve shown in a closed position.
Figure 6B:
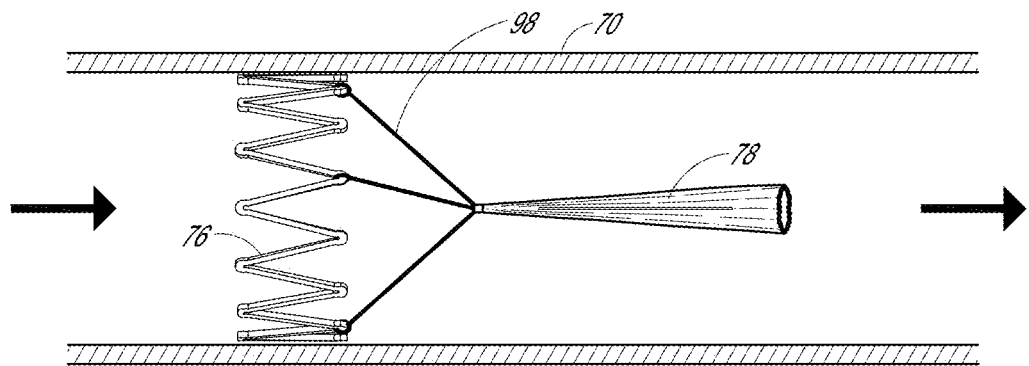
FIG. 6B is a side elevational view of the valve of FIG. 6A, shown in an open position.

Referring to FIGS. 6A and 6B, there is illustrated a modification of the wind sock valve discussed above. In this illustration, the occluder 78 is mounted "off board" from the support structure 76, and secured against axial relative movement by a plurality of struts 98. In this construction, the occluder 78 is preferably provided with at least one or two or three or more longitudinal extending ribs 100, in the nature of a sail batton. The battons allow the occluder 78 to reciprocate between the closed configuration of FIG. 6A and open configuration of FIG. 6B, in response to blood flow, without axial collapse or prolapse of the conical occluder membrane. The battons may be secured to an inner or outer surface of the membrane forming the occluder, or may be entrapped between an inner membrane and an outer membrane which are bonded together to form the finished occluder.

Figure 7A:
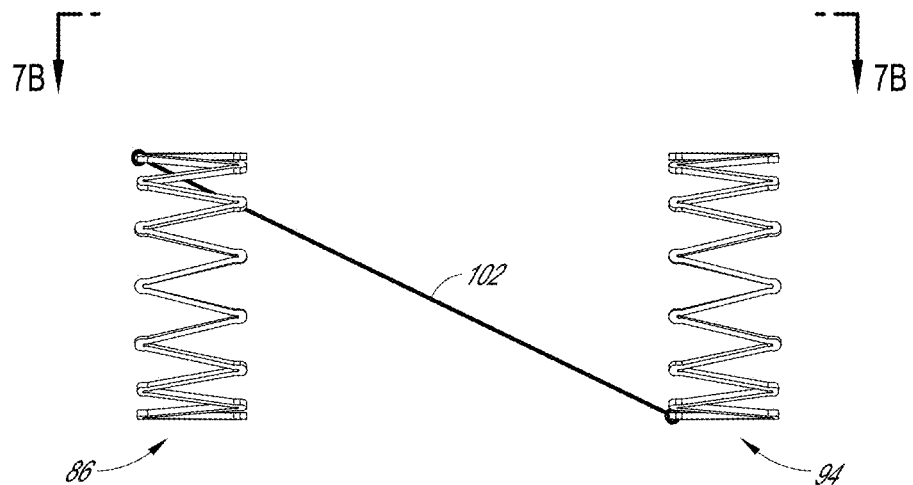
FIG. 7A is a side elevational view of a frame for an alternate valve configuration.

Referring to FIG. 7A, there is illustrated a side elevational view of an alternate implant in accordance with the present invention. In the illustrated embodiment, a first tubular support 86 and a second tubular support 94 are connected by a backstop 102. A single tubular support may alternatively be used, which may extend approximately equal to the axial length of the backstop 102, or less than or greater than the axial length of the backstop 102.

Figure 7B:
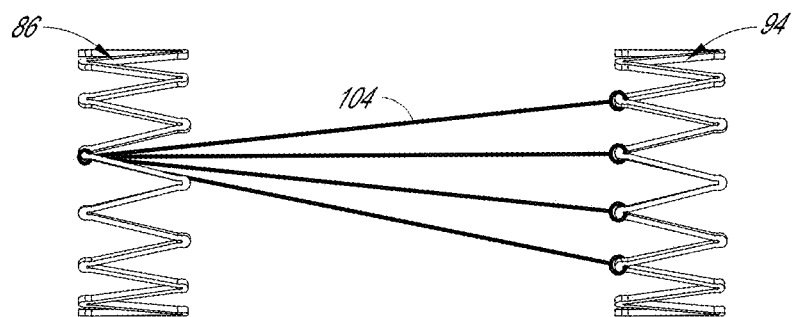
FIG. 7B is a top plan view of the frame shown in FIG. 7A.
Figure 7C:
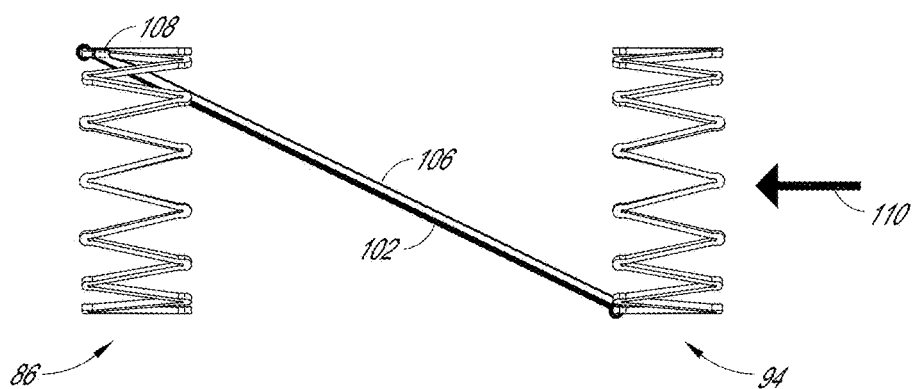
FIG. 7C is a side elevational view of the frame as in FIG. 7A, together with an occluder and shown in a closed configuration.
Figure 7D:
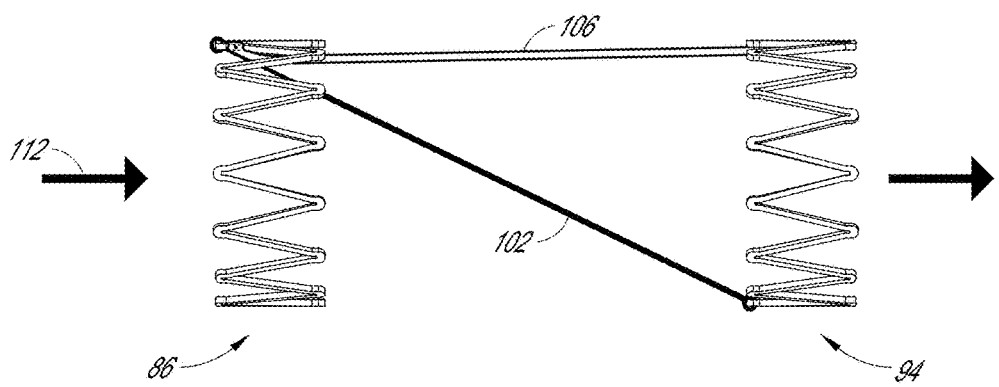
FIG. 7D is a side elevational view as in FIG. 7C, with the occluder in an open position.

Referring to FIG. 7B, there is illustrated a top plan view of the implant of FIG. 7A, illustrating the backstop as at least one and preferably a plurality of struts 104 which extend at a diagonal across the blood flow lumen to permit blood flow therethrough. As illustrated in FIG. 7C, the backstop 102 serves to support an occluder membrane 106. The occluder membrane 106 is secured at least at an attachment point 108 with respect to the tubular support. As illustrated in FIG. 7C, retrograde blood flow in the direction 110 pins the occluder membrane 106 against the backstop 102, thereby inhibiting further retrograde blood flow. As illustrated in FIG. 7D, antegrade blood flow in the direction 112 flows through the struts 104 of the backstop 102, and pushes the occluder 106 against the wall of the lumen, permitting forward blood drainage towards the heart.

Figure 7E:
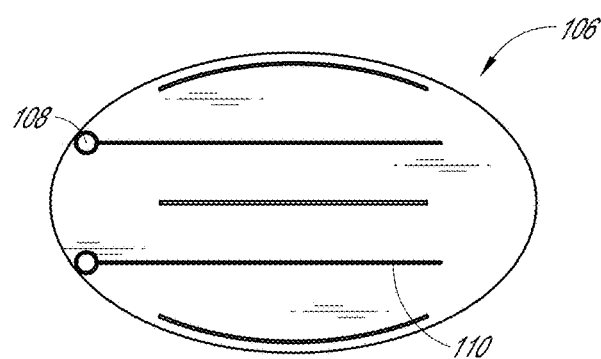
FIG. 7E is top plan view of an occluder useful in the frame in FIG. 7A.

In one implementation of the invention, the occluder 106 comprises a substantially oval shaped profile, such that it approximately conforms to the wall of the lumen when in the occlusive orientation illustrated in FIG. 7C. See FIG. 7E. The occluder 106 may be provided with one or more attachment points 108 for flexible or pivotable attachment to the support structure. In the illustrated implementation, attachment structure 108 may comprise an eyelet on one end of an elongate wire or polymeric batton 110. At least one, and often at least two or three or more battons 110 are provided, spaced apart and generally parallel to the major axis of the oval. In this manner, the structural integrity of the occluder 106 may be maintained, while at the same time preserving flexibility of the occluder 106 to bend into an arc about an axis which is parallel to its longitudinal axis, such that it may conform to the inner surface of the vessel wall when in the open configuration illustrated schematically in FIG. 7D. As has been previously discussed, the occluder 106 may comprise any of a variety of thin film membranes, such as ePTFE, or tissue such as pericardium may alternatively be used. In one embodiment, the battons 110 comprise elongate polymeric elements sandwiched between a first and second layer of ePTFE. The facing ePTFE surfaces may be provided with a bonding layer such as FEP, so that the composite stack may be heated under pressure to produce the finished occluder 106.

Figure 8A:
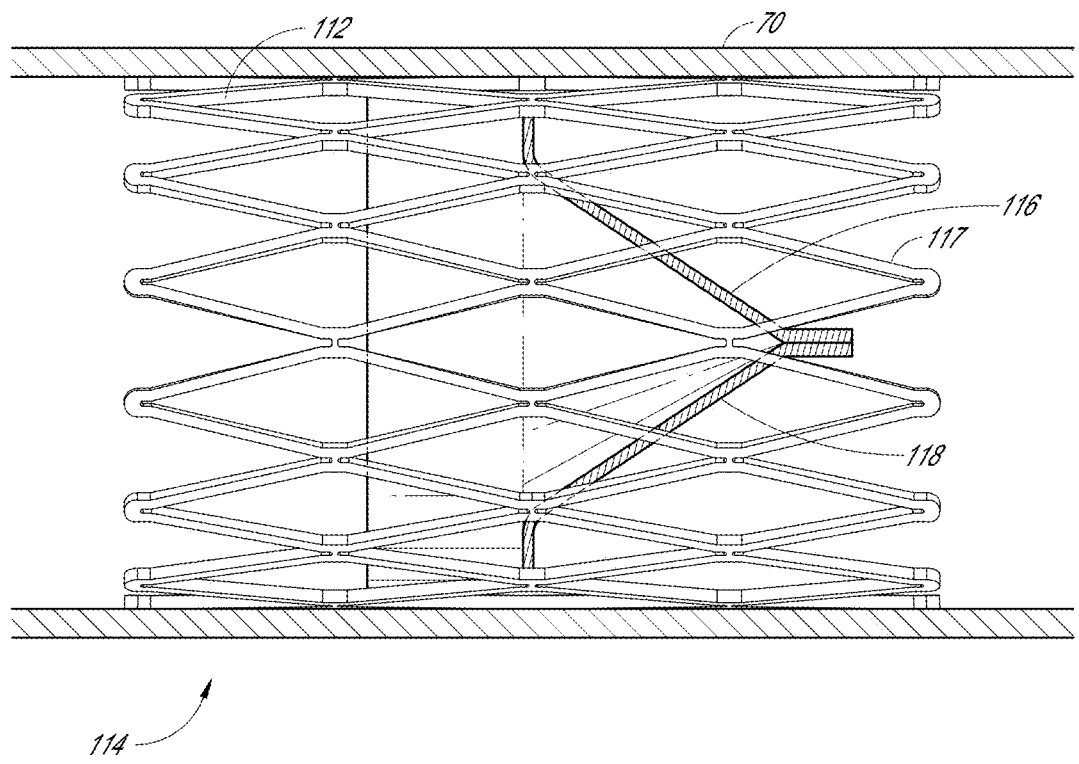
FIGS. 8A and 8B are side elevational views of stents having a bi-leaflet or duckbill valve therein.
Figure 8B:
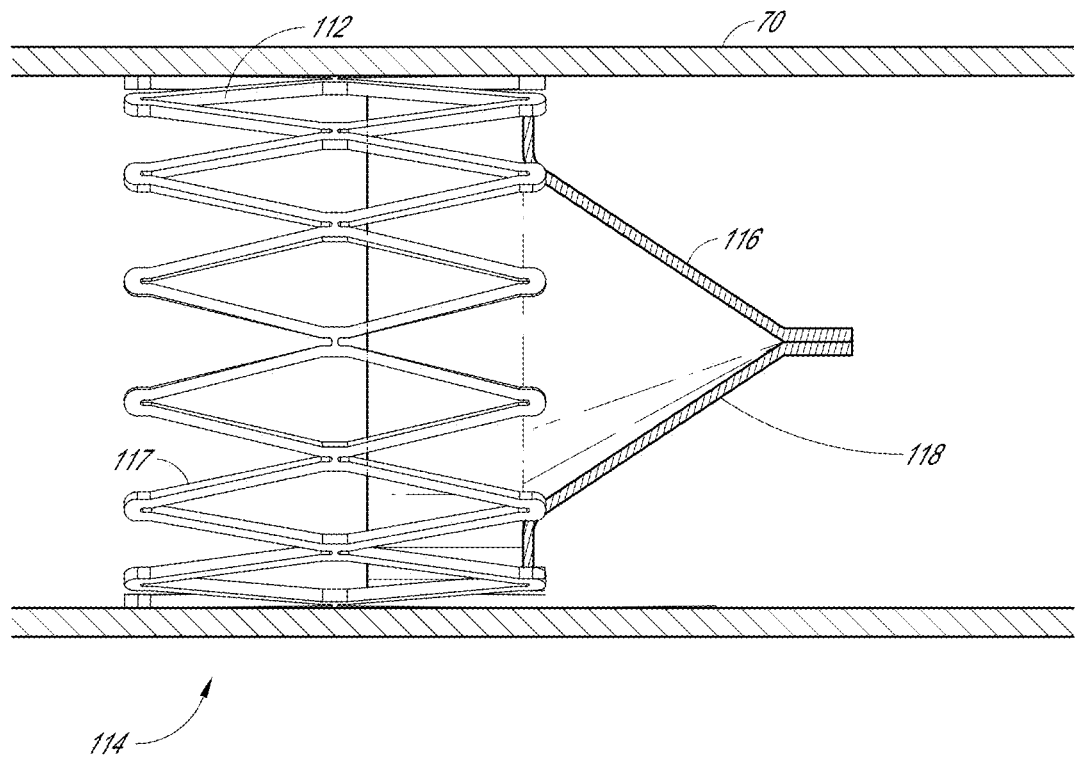

Any of a variety of alternative valve construction may be utilized, depending upon the desired performance result. For example, referring to FIG. 8, there is illustrated a schematic view of a simple bi-leaflet duck bill valve 114. A support structure such as a balloon expandable or self-expandable stent 112 is illustrated positioned within a vessel 70.

In the illustrated embodiment, the valve 114 comprises a first leaflet 116 coaptively engaged with a second leaflet 118 to enable flow in a single direction. Single leaflet, bi-leaflet, tri-leaflet or other valves may be utilized, although bi-leaflet or tri-leaflet may be preferred. Suitable valves may be harvested from porcine, bovine, canine or other animal sources known in the art, or may be constructed such as from bovine, porcine or human tissue. The harvesting, treatment and use, for example, of pericardium is well understood in the prosthetic heart valve arts, and not disclosed in detail herein. Alternatively, autologous valves such as venous valves harvested from the peripheral vasculature of a patient may be prepared and deployed in accordance with the present invention.

The support structure for the venous valves in accordance with the present invention function to support the valve in an operative orientation within the vein, and resist migration away from the deployment site. A stent or stent like tubular structure is one convenient form of a support, and provides the basis for much of the discussion herein. However, structures which do not resemble a conventional stent may alternatively be used.

Figure 9A:
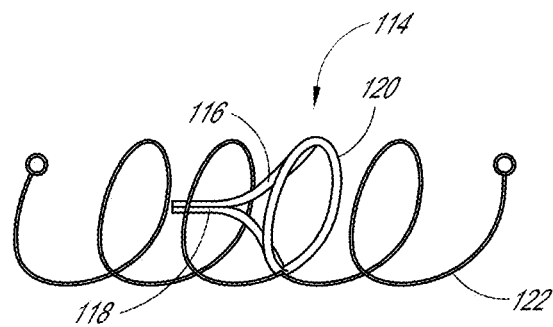
FIG. 9A is a side elevational view of a valve carried by a helical coil support structure.

For example, referring to FIG. 9A there is illustrated a valve 114 having an annulus 120 connected to a support structure 122. Support structure 122 comprises an elongate flexible element such as a wire, which extends in a helical loop in contact with the vascular wall. One or two or more loops may extend in a downstream flow direction from the annulus 120 and or one or two or more loops may extend in an upstream flow direction from the annulus 120. The annulus 120 may be supported by a loop of the support structure 122, and leaflets 116 and 118 may be secured such as by suturing to the annulus 120. The spiral or pigtail loop anchors may be formed from any of a variety of materials including metal wire such as Nitinol, which enables collapse to a relatively low crossing profile during deployment and self-expansion to fit within the vessel.

Figure 9B:
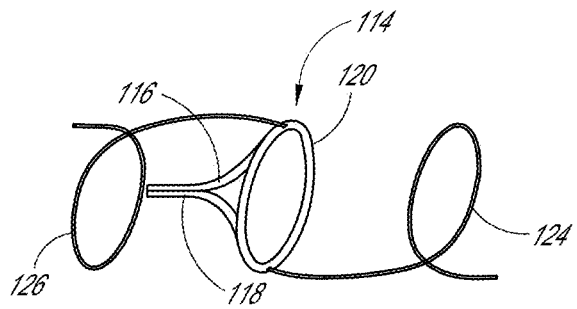
FIG. 9B is a side elevational view of a valve having upstream and downstream pigtail anchors.

A variation is illustrated in FIG. 9B, in which a pigtail or haptic like anchor 124 is provided upstream of the valve 114 and a second pigtail anchor 126 is provided downstream of the valve 114. Each anchor extends in a spiral through no more than about one or two complete revolutions along the vessel wall. In any of the supports disclosed herein, two or three or more axially extending commissural supports may be added as needed, and secured relative to annulus 120, such as three commissural supports if a tri-leaflet tissue valve is used.

Figure 9C:
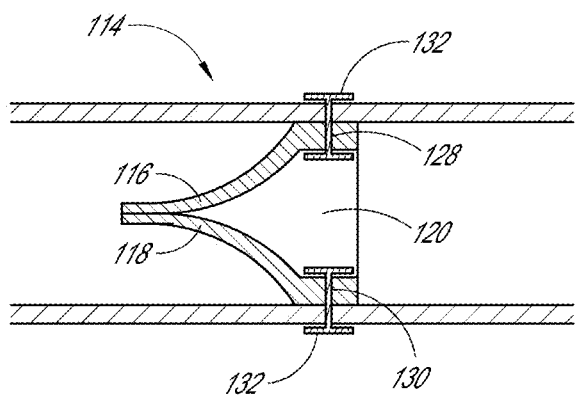
FIG. 9C is a side elevational view of a valve coupled directly to the vessel wall with tissue penetrating anchors.

Referring to FIG. 9C, there is schematically illustrated a stentless valve system, in which the annulus 120 or a structure secured to the annulus 120 is directly attached to the vessel wall. Attachment may be accomplished utilizing any of a variety of tissue penetrating structures, such as sutures, clips or barbs, configured for deployment from a catheter. In the illustrated embodiment, at least a first tissue penetrating anchor 128 extends from the annulus 120 into the vessel wall. The tissue penetrating anchor may be provided with a transverse element for placement against the extravascular surface, such as a "T" tag 132 as is known in the art. At least a second tissue penetrating anchor 130, which may additionally be provided with a transverse distal element may additionally be provided. At least two or four or six or more tissue penetrating anchors may be utilized for each valve, depending upon the desired performance.

Figure 10A:
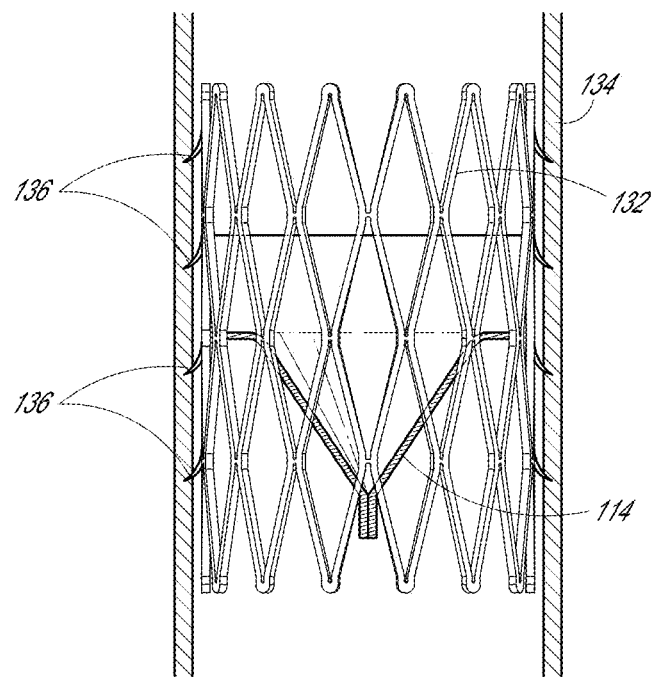
FIG. 10A is a side elevational view of a valve carried by a stent which is provided with a plurality of tissue barbs.

In any of the stent or other support structure systems disclosed herein, any of a variety of features may be added to inhibit migration within the vessel. For example, referring to FIG. 10A, a valve 114 is schematically illustrated as a bi-leaflet valve. The valve 114 is supported by a support structure 132, such as a tubular stent. The support structure 132 is deployed within a vessel wall 134. A plurality of tissue engaging structures such as barbs 136 extend from the support 132 into the wall of the vessel. Barbs 136 may extend transversely to the longitudinal axis of the vessel, or may be inclined in an antegrade or a retrograde flow direction.

Figure 10B:
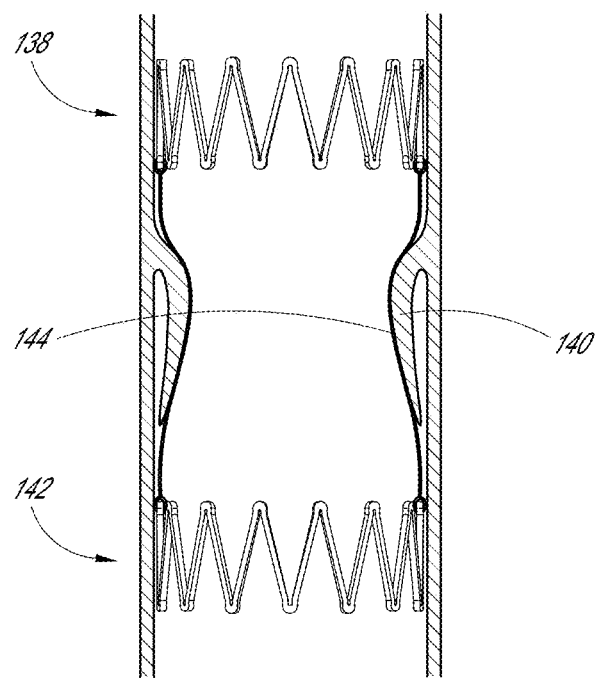
FIG. 10B is a side elevational view of an implant which straddles the native valve.

Referring to FIG. 10B, an implant is illustrated in which a first portion 138 of the support is positioned on a first side of a native valve 140 and a second portion 142 of the support is positioned on a second side of the native valve 140. A prosthetic valve (not illustrated) may be carried by the support construct at any point along the length of the implant. At least one, and preferably two, or three or more axially extending elements 144 link the first portion 138 and the second portion 142 such that the construct spans the native valve, which serves as an anchor against axial migration. Tissue penetrating elements or other surface structures may additionally be utilized, as desired.

Figure 10C:
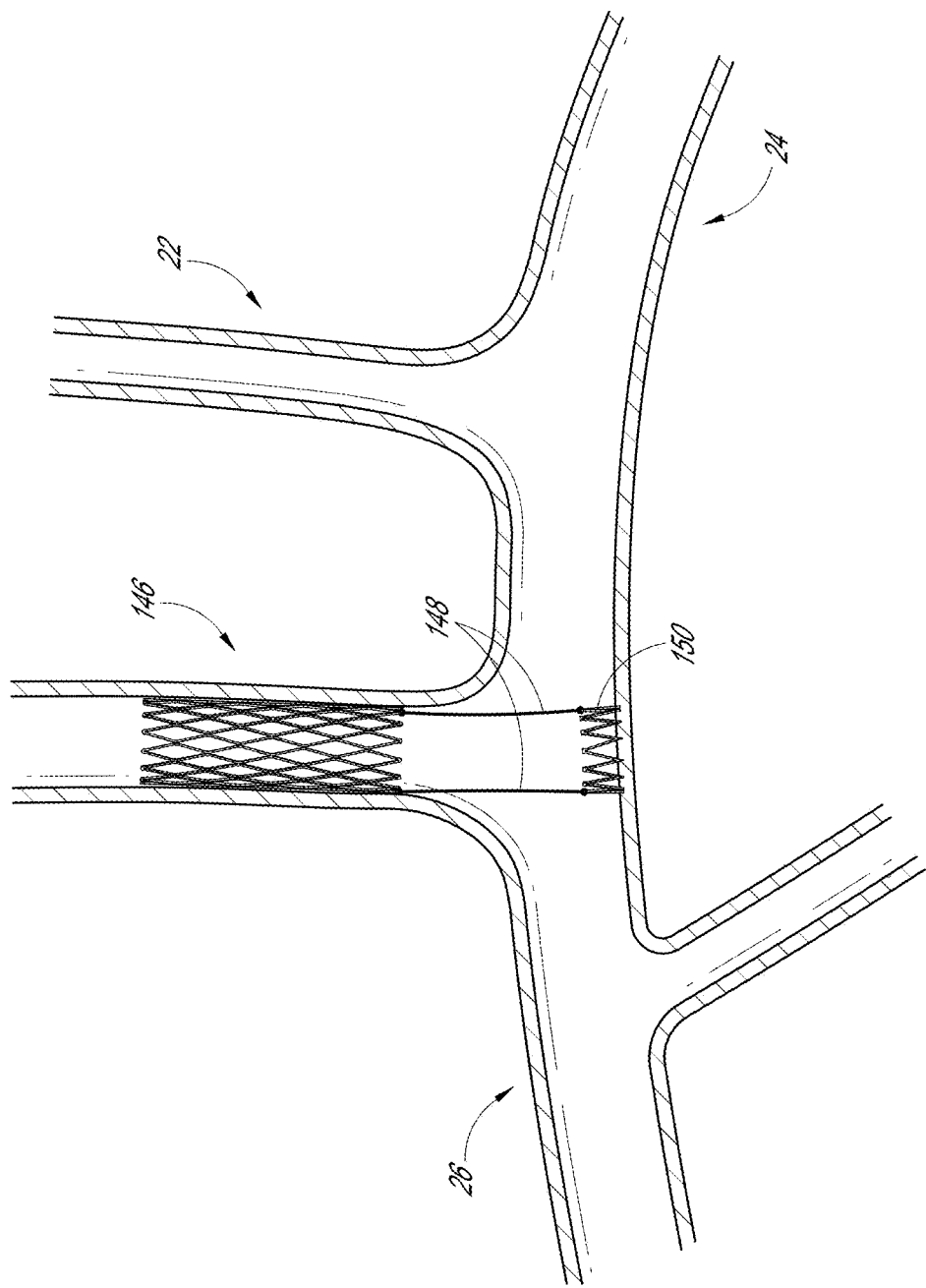
FIG. 10C is a schematic view of a valve support positioned within the left internal jugular, and supported by the opposing wall of the subclavian vein.

The anchor system may also be customized to unique anatomical environments. For example, FIG. 10C illustrates an embodiment which may be useful in anatomy such as the left internal jugular or external jugular, which may join the subclavian vein at a nearly perpendicular angle. A tubular support 146 may be positioned in the left internal jugular, having at least one valve thereon to replace native valve function. The support 146 is provided with a base 150 which establishes a footprint against the wall of the subclavian vein opposing the ostium to the left internal jugular. The base 150 may be spaced apart from the support 146, such as by one or two or four or more struts 148. Struts 148 are configured to resist downstream migration of the support 146, yet permit transverse venous flow from the subclavian into the left innominate vein.

Figure 10D:
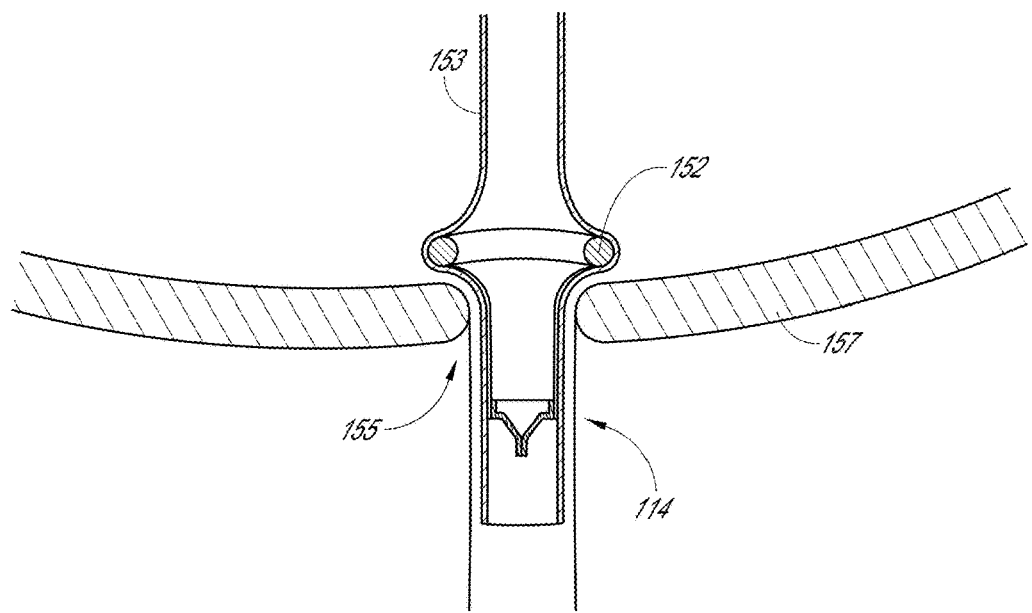
FIG. 10D is a schematic view of a valve supported by an extra vascular boney structure.

Referring to FIG. 10D, the support structure may also cooperate with one or more extra vascular structures, to resist migration within the vein. The valve 114 in FIG. 10D is provided with an annular structure 152 such as the valve annulus or other radially outwardly projecting support structure attached to the annulus, having a first, deployed outside diameter measured transverse to blood flow. The vein 153 extends through an anatomical structure such as a foramen 155 in the base of the skull 157, having a second diameter which is smaller than the first diameter. This enables the valve to hang from the anatomical structure without migration.

Figure 10E:
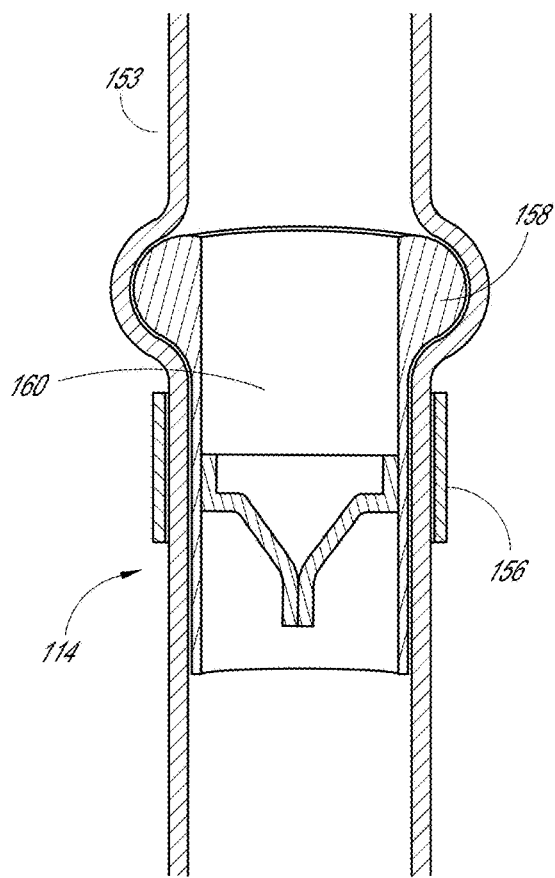
FIG. 10E is a schematic view of a valve supported by an extra vascular cuff.

Migration may also be inhibited through the use of one or more extra vascular structures, which provide an interference fit through the venous wall with a component on the valve to inhibit migration. Referring to FIG. 10E, an extra vascular structure such as an annular cuff 156 establishes an inside diameter within the vein, which cannot be exceeded under normal environmental conditions. Extra vascular cuff 156 may comprise any of a variety of structures, such as a metal or polymeric ring, mesh, suture loop, or other structure, most readily implanted via direct surgical access.

A radially outwardly extending element such as a projection, flange or annulus 158 is provided on the implant 160. The outside diameter of the annulus 158 plus the wall thickness of the vein 153 exceeds the inside diameter of the extra vascular cuff 156, thereby inhibiting downstream migration of the valve.

In accordance with the method of the present invention, a patient is identified having an obstruction in the venous outflow track from the brain. The obstruction may be identified using doppler ultrasound in accordance with techniques well understood in the art. The doppler ultrasound may be accomplished on patients with a clinical diagnosis of transient global amnesia, multiple sclerosis, or any of a variety of symptoms associated with multiple sclerosis, such as paresthesias, numbness, limb weakness, double vision, visual loss, complete local motor dependency, urine incontinence and cognitive decline. Doppler ultrasound may be performed on patients diagnosed with multiple sclerosis, in any of the three main clinical courses of relapsing remitting, secondary progressive, and primary progressive. Evaluation may include sonographic (extracranial echo color-doppler and transcranial color-doppler ultrasound) evaluation.

Once a stenotic lesion as been identified, percutaneous access to the venous vasculature may be achieved for example at the femoral vein, and a balloon dilatation catheter may be advanced over or along a guidewire to position the balloon within the lesion. The lesion is thereafter dilated, the balloon deflated and removed in accordance with techniques well understood in the art.

In certain implementations of the invention, dilation is accompanied by placement of an intravascular stent, without implantation of a valve.

In an alternative implementation of the invention, the dilation is followed by placement of a valve, carried by a support structure such as a stent. In general, stenotic lesions which are spaced apart from the native valves, may be dilated and supported with an intravascular stent in the absence of implantation of a valve. However, lesions involving a valve, or other valvular dysfunction may suggest the desirability of implantation of one or more valves of the type disclosed previously herein.

In one example, one or two valves in the left internal jugular have become undesirably resistive to forward blood flow. The valve is accessed via conventional techniques, and a valvuloplasty is accomplished by dilation of a balloon or other expansion structure within the valve to restore patency to the lumen. The valvuloplasty catheter may comprise a bare balloon, or a balloon which carries an intravascular support such as a stent. A valve may be associated with the intravascular support.

Alternatively, the valvuloplasty balloon may be utilized to deploy a stent or other support structure in the vicinity of the dilated valve simultaneously with valve dilatation. The valvuloplasty balloon catheter is removed from the patient, and a valve deployment catheter is thereafter positioned within the deployed support. A valve carried by the valve deployment catheter is coupled to the support, and the valve delivery catheter is proximally retracted from the patient leaving the valve coupled to the support at the treatment site.

Figure 11:
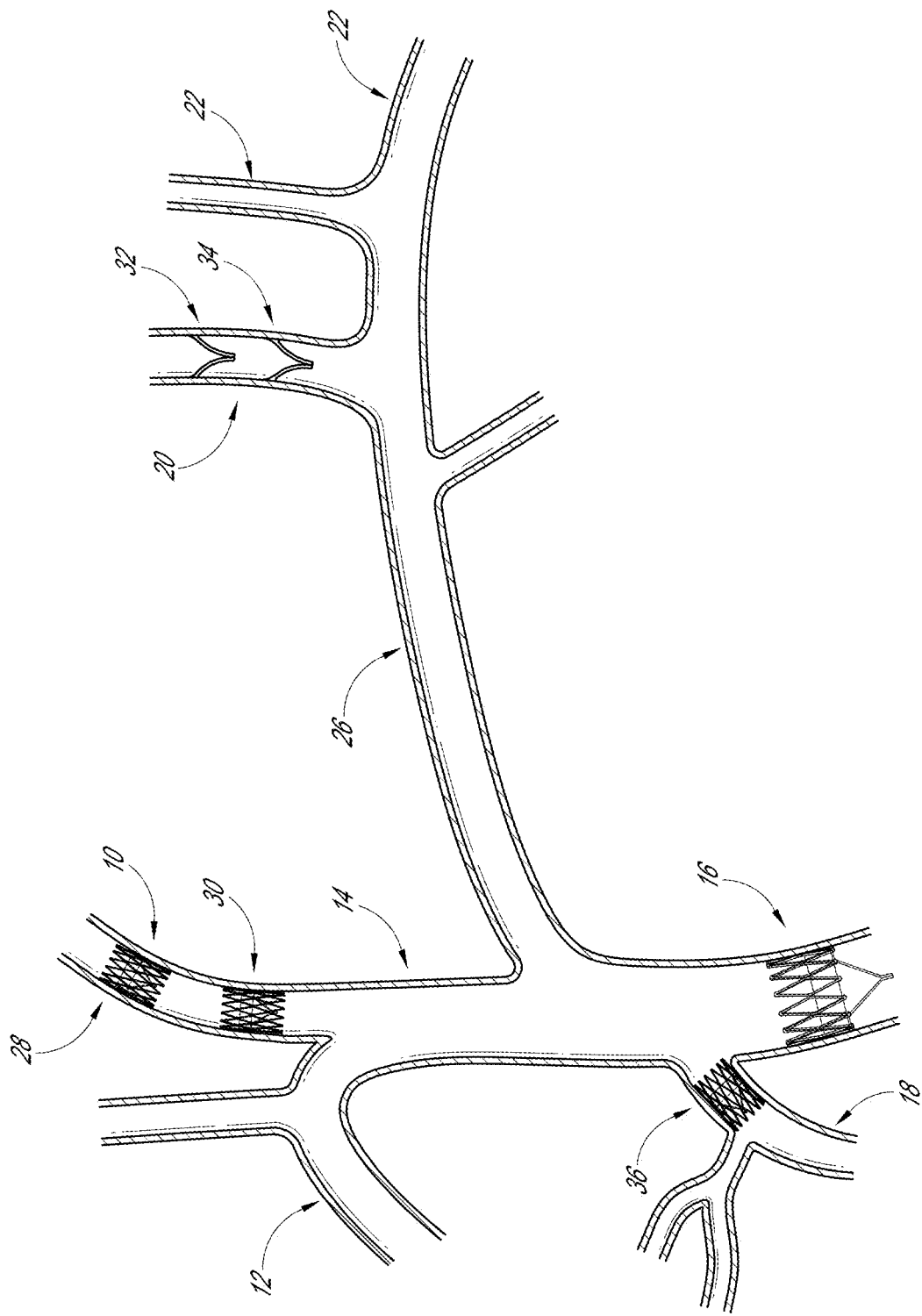
FIG. 11 is a schematic view of a valve positioned within the superior vena cava.

It is believed that the implanted valve need not necessarily reside at the same location as the native valve. Thus, a valve and valve support structure may be deployed within the vasculature, spaced apart from the dilated valve. Balloon dilatation of valves in the right internal jugular, for example, may therefore be followed by placement of a valve in either the right internal jugular or the right innominate vein. Similarly, balloon dilation of one or more valves in the left internal jugular may be followed by implantation of one or more valves in the left internal jugular or the left innominate vein. As a further alternative, balloon dilation, with or without stenting, of any of a variety of valves in the venous outflow track from the brain may be followed by positioning of a valve in the superior vena cava. For example, referring to FIG. 11 there is disclosed a valve carried by a support structure such as a stent and positioned within the superior vena cava. As illustrated, the valve is positioned in between the ostium to the azygos vein and the heart. The valve may alternatively be positioned between the azygos vein and the bifurcation of the right and left innominate vein.

Figure 12:
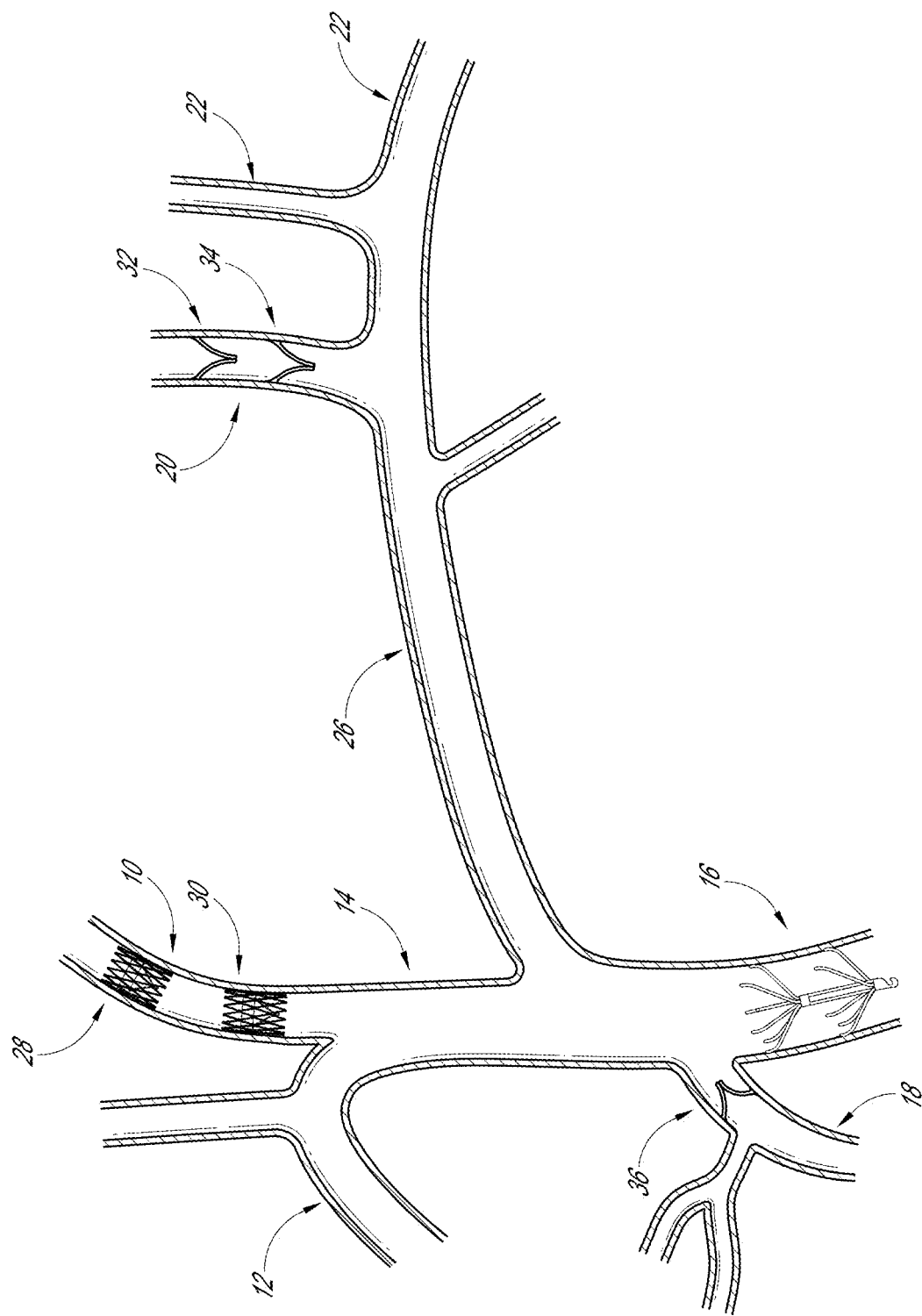
FIG. 12 is a schematic view of an embolic filter positioned within the superior vena cava.

In addition to any of the foregoing, it may be desirable to implant a filter in the flow path between the treatment site and the heart, if a risk of embolization to the heart is a concern. Thus, referring to FIG. 12, there is illustrated a vena cava filter positioned within the superior vena cava. Any of a variety of filters presently configured for deployment within the inferior vena cava may be adapted for use in this environment, and may be any of a variety of self-expandable frame or frame and mesh structures.

Either as an alternative to or in addition to any of the foregoing percutaneous or minimally invasive procedures, methods and devices in accordance with the present invention can also be optimized for surgical intervention. Thus, referring to FIG. 13, there is illustrated an extravascular valved venous graft 200. The venous graft 200 has been anastomosed to the native vasculature to place a superior opening 202 in fluid communication with an inferior opening 204 to bypass one or both of venous valves 32 and 34. In the illustrated implementation, valve 32 and 34 are both partially or fully obstructed by thrombus or other condition 206.

The extravascular valved venous graft 200 comprises an elongate flexible tubular body 208 extending between a superior end 210 and an inferior end 212. Superior end 210 is provided with an end to side anastomosis 214 to the left internal jugular vein, utilizing sutures 216 or other clips or attachment techniques known in the art. Inferior end 212 of tubular body 208 is connected via anastomosis 218 at the inferior opening 204 to the left innominate vein 26. Tubular body 208 thus provides a bypass conduit for cerebral venous drainage, avoiding the obstruction 206.

Tubular body 208 may be provided with at least a first valve 220, and, optionally, at least a second valve 222. Any of a variety of valves structures such as those disclosed elsewhere herein may be utilized. Tubular body 208 may comprise any of a variety of materials suitable for use in vascular grafts, such as ePTFE, Dacron, or other fabric or extrudable polymers. The tubular body 208 may be supported along at least a portion or the entire length thereof to maintain patency of the graft 200. Any of a variety of support structures may be utilized, such as an end-to-end construct of Z stent structures as has been disclosed elsewhere herein. Alternatively, since the endovascular valved venous graft 200 is intended for surgical implantation, the ability to collapse and expand may not be necessary. Thus, any of a variety of reinforcing structures such as a plurality of axially spaced apart annular rings or hoops, or a helical wire or polymeric filament support may be attached to the interior surface or the exterior surface of the graft 200, or entrapped between an inner tubular layer and an outer tubular layer. Techniques for surgical implantation and anastomosis of bypass grafts are well understood in the coronary and peripheral vasculature, and will not be detailed further herein.

Figure 13:
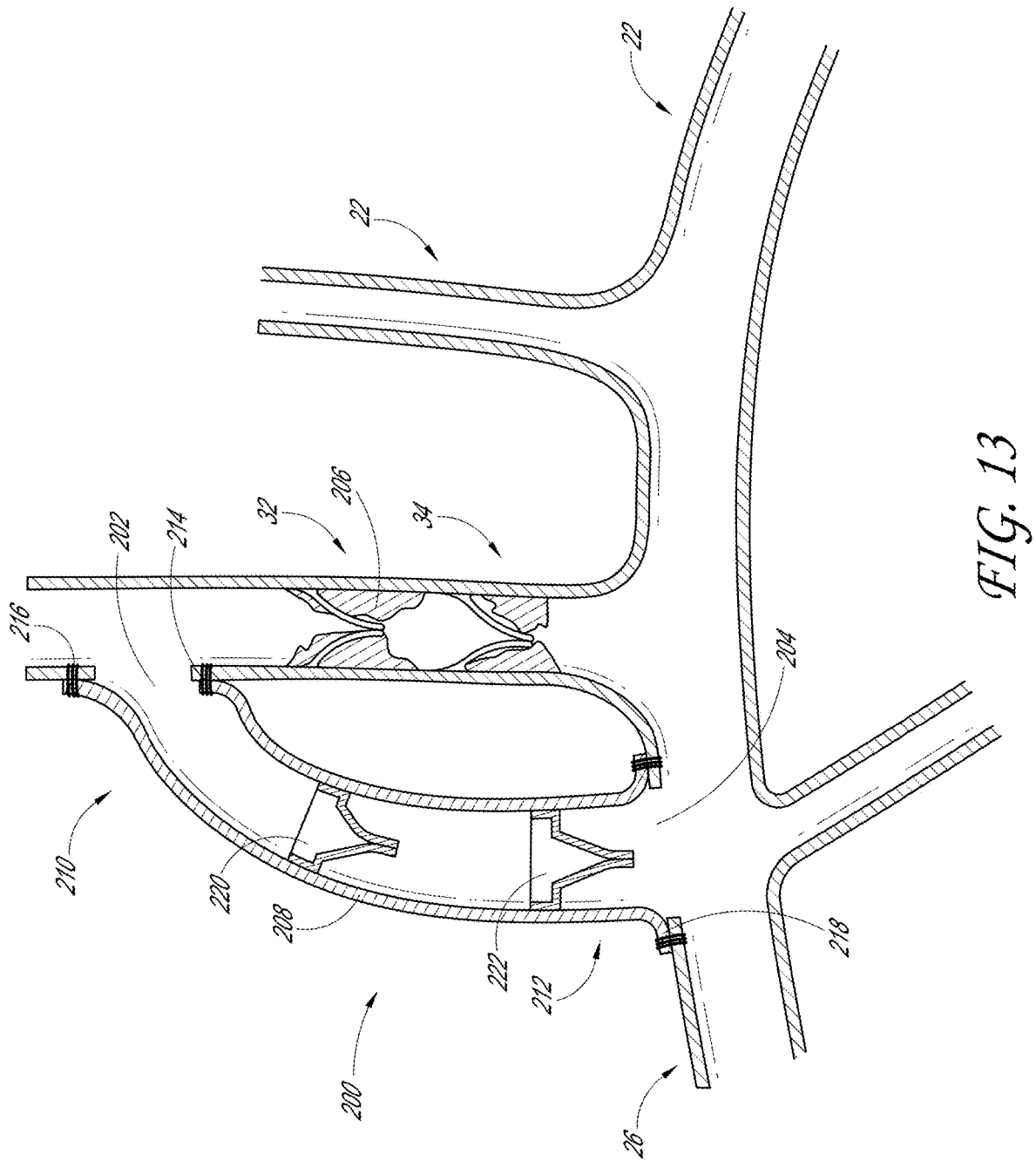
FIG. 13 is a schematic view of a valved extravascular graft shown attached via anastomosis to the left internal jugular and the left innominate veins.
Figure 14:
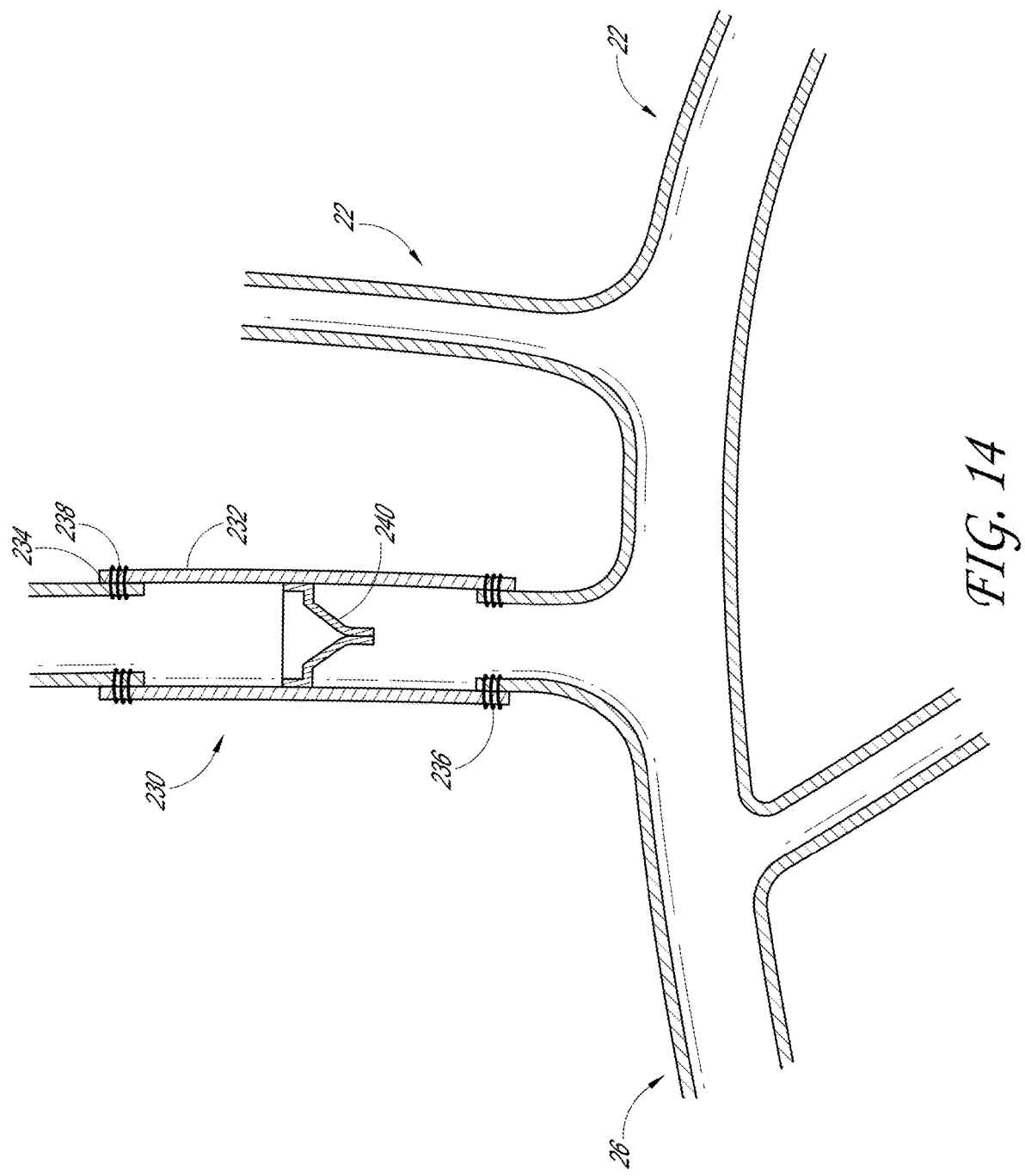
FIG. 14 is a schematic view of a valved graft implanted to replace a section of the left internal jugular.

As an alternative to extravascular bypass as illustrated in FIG. 13, an occluded segment of vein can be severed, and completely removed from the vasculature. Depending upon the length of the occlusion, the free ends of the remaining vasculature may be brought together and anastomosed to provide fluid flow with or without insertion of a prosthetic valve. Alternatively, as illustrated in FIG. 14, a valved vascular graft 230 may be used to replace the removed segment of vein. The graft 230 comprises an elongate flexible tubular body 232 having at least one valve 240 illustrated as replacing a segment of the left internal jugular from which a section of vein having one or more vein valves has been removed. Tubular body 232 is connected via a superior anastomosis 234 and an inferior anastomosis 236 using sutures 238 or other attachment techniques known in the art. The graft 230 may be supported along a portion or all of its length, and may otherwise be provided with any of the features described previously in connection with extravascular valved venous graft 200.

As an alternative to the prosthetic grafts described above, native tissue (typically autologous) can be harvested, prepared and implanted in accordance with the methods of the present invention. Thus, either of the valved grafts 200 (of FIG. 13) or 230 (of FIG. 14) can be formed from a section of a vein such as the saphenous vein, including at least one valve, which can be harvested in accordance with known techniques and surgically implanted in accordance with the methods described previously herein.

Hybrid procedures may also be utilized, such as balloon valvuloplasty of a valve in the venous outflow track from the brain, followed by surgical access to implant a prosthetic valve. Any of a variety of valve configurations may be utilized for surgical implantation, as will be appreciated by those of skill in the art. For example, a valve adapted for surgical implantation is illustrated in FIGS. 15A & 15B. Valve 114 comprises a first leaflet 116, a second leaflet 117 and a third leaflet 118 although bi-leaflet valves may alternatively be used. The leaflets are supported by an annulus 120, as is understood in the art. Annulus 120 may comprise a native tissue annulus, in a valve such as a porcine or bovine valve. A tissue annulus 120 may be secured directly to the vein, such as by sutures.

Alternatively, in a prosthetic valve such as one in which the leaflets comprise a polymeric membrane or tissue such as pericardium, the annulus 120 may comprise a biocompatible metal or polymer. In this instance, a fabric coating 121 such as a Dacron or ePTFE sleeve may be provided over the annulus 120, to form a sewing ring such that sutures can be stitched through the fabric 121 into adjacent venous tissue.

Alternatively, the valve 114 may be supported within a length of tubular graft 250, as schematically illustrated in FIG. 16. Valve 114 may be sutured or otherwise secured to the section of graft 250, which provides a convenient attachment structure for attachment to the vein. Graft 250 may comprise any of a variety of materials discussed previously herein, such as ePTFE or Dacron. The annulus 120 of valve 114 may be secured directly to the graft 250, such as by sutures, adhesives, clips or other attachment technique. Alternatively, an optional stent 114 may be provided, to secure the valve and/or support the graft 250 and maintain patency in the vicinity of the valves. First end 252 and second end 254 of graft 250 may be attached directly to the vein. The axial length of graft 250 will typically be at least about 1 cm or 2 cm, and often at least about 5 cm. Graft 250 may be provided in lengths of at least about 10 cm or 20 cm, and the implantation step may include the step of cutting the graft 250 to a desired length prior to surgically attaching the graft 250 to the native vasculature. At least one or two or three or four or more valves 114 may be provided within graft 250.

In accordance with a further aspect of the present invention, there is provided a formed in situ valve. Formed in situ valves may be constructed either translumenally, surgically or a combination of both.

Referring to FIGS. 17-19B, formed in situ valve 258 is formed in a section of vessel 260. Vessel 260 may be a segment of vein, such as any of the veins described previously herein. Alternatively, vessel 260 may comprise any of a variety of other tubular organs or vessels such as arteries.

Vessel segment 260 defines a central flow lumen 261 which permits blood flow in a downstream flow direction 263. Flow thus extends from an upstream side 262 to a downstream side 264 of the valve.

Figure 17A:
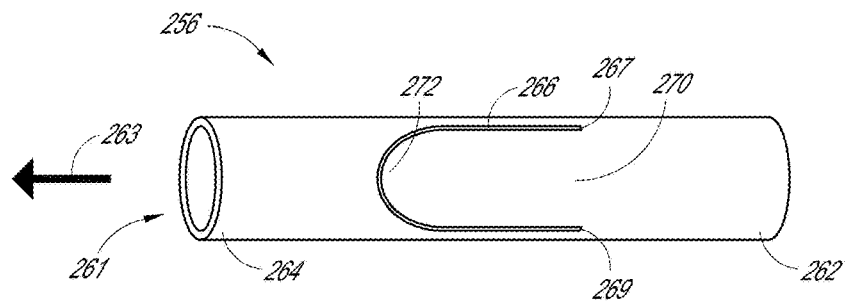
FIG. 17A is a top plan view of a vein having a flap formed therein.
Figure 17B:
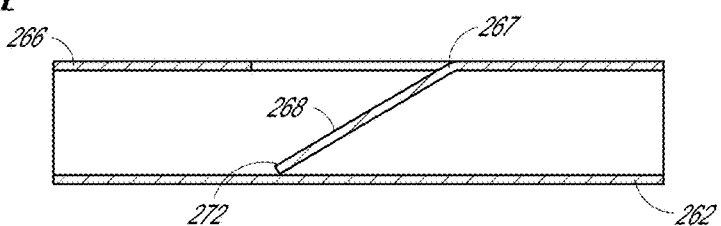
FIG. 17B is a cross-sectional elevational view of the section of vein shown in FIG. 17A, with the flap in an occlusive orientation.

The valve is formed by creating an incision 266 having a generally U shape, such that a first end 267 and second end 269 of incision 266 are oriented in a relative upstream direction, and a free end 272 is oriented in a downstream direction. Incision 266 thus creates a flap 268 which remains connected to the vessel 260 via a hinge 270. This construction enables the flap 268 to pivot about the vicinity of the hinge 270 and close the central lumen 261 as illustrated in FIG. 17B. Flap 268 may be most conveniently formed through surgical procedures, although transluminal devices may be devised to construct the flap 268.

Figures 18A, 18B:
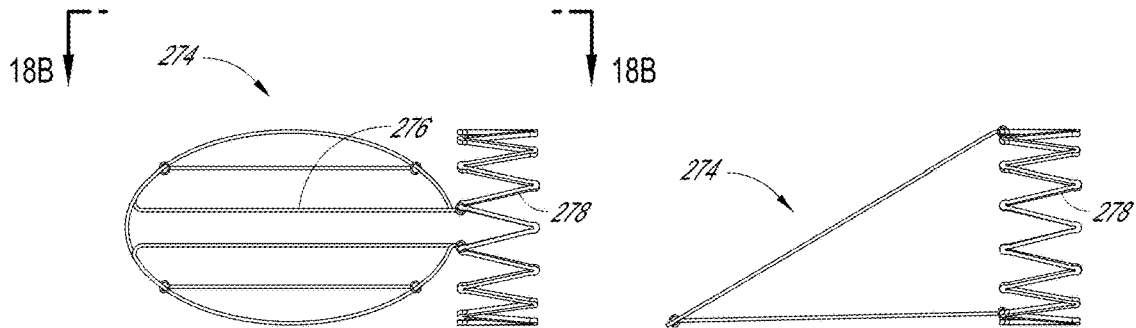
FIG. 18A is a top plan view of a backstop for limiting movement of the tissue flap.
FIG. 18B is a side elevational view of the backstop illustrated in FIG. 18A.

Due to the thin nature of the venous wall, a flap 268 in the presence of reverse direction blood flow may well be carried in an upstream direction beyond the hinge 270 and not provide any valving function. Thus, a backstop 274 which comprises a limit surface such as a plurality of spaced apart struts 276 may be positioned within the vessel, to limit upstream movement of the flap 268 beyond a closed orientation. Backstop 274 may be integrally formed with or attached to a support 278 which may comprise any of a variety of balloon expandable stents, self-expandable stents or other attachment structures such as those disclosed elsewhere herein. Backstop 274 may be introduced into the vessel either via the incision 266 in a surgical procedure, or translumenally via a remote vascular access site. As illustrated in FIG. 18B, backstop 274 provides a surface which resides at an angle with respect to the longitudinal axis of the vessel 260. The angle may be anywhere within the range from about 90° to about 35° or 40°, depending upon the diameter of the vessel, length of the flap 268 and desired performance characteristics.

Figure 19A:
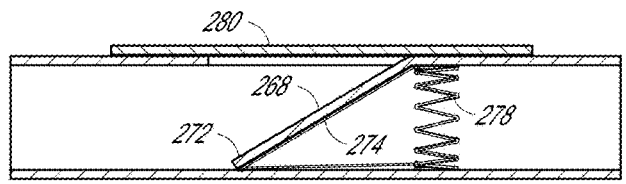
FIG. 19A is a side elevational schematic view of a formed in situ valve, in a closed configuration.
Figure 19B:
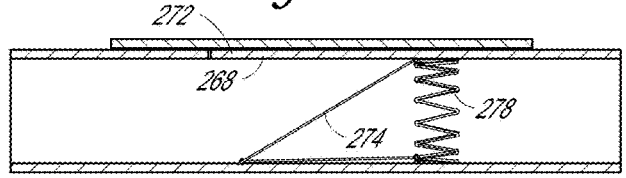
FIG. 19B is a side elevational view of the valve of FIG. 19A, in an open configuration.

Since the flap 268 functions as the occluder in the formed in situ valve 258, when the flap 268 is in the "closed" orientation as in FIG. 17B, venous flow would escape via incision 266. Thus, referring to FIG. 19A, a patch 280 is positioned over the incision 266 to enclose the lumen 261, and permit flap 268 to reciprocate between an occlusive or closed orientation as in FIG. 19A, and an open or forward flow orientation as illustrated in FIG. 19B. The patch may comprise any of a variety of materials, such as autologous tissue (e.g. pericardium), or any of a variety of fabrics or mesh such as Dacron or ePTFE. Patch 280 may be sutured to the vein wall, attached using clips, adhesives, extravascular annular cuffs or other structures for surrounding the patch and the vein.

Any of the valves or valve supports deployed in accordance with the present invention may be coated with or otherwise carry a drug to be eluted over time at the deployment site. Any of a variety of therapeutically useful agents may be used, including but not limited to, for example, agents for inhibiting restenosis, inhibiting platelet aggregation, or encouraging endothelialization. Some of the suitable agents may include smooth muscle cell proliferation inhibitors such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagnonist, and 5-HT uptake inhibitors; cholesterol-lowering agents; vasodilating agents; and agents which interfere with endogeneus vascoactive mechanisms. Polynucleotide sequences may also function as anti-restenosis agents, such as p15, p16, p18, p19, p21, p2'7, p53, p5'7, Rb, nFkB and E2F decoys, thymidine kinase ("TK") and combinations thereof and other agents useful for interfering with cell proliferation. The selection of an active agent can be made taking into account the desired clinical result and the nature of a particular patient's condition and contraindications. With or without the inclusion of a drug, certain of the valve supports disclosed herein can be made from a bioabsorbable material. Various polymeric carriers, binding systems or other coatings to permit controlled release of active agent from the valve or support or its coating are well known in the coronary stent arts and not reproduced herein.

Additional treatment systems and methods of use for application in patients suffering from Multiple Sclerosis caused by insufficient venous capacity are described below. This treatment is particularly challenging due to the large size and compliance of veins and the resulting in the potential stent migration. Furthermore, some lesions within the venous vasculature can be very fibrotic and difficult to open with standard PTA balloons. More aggressive dilatation devices such as the cutting balloon from Boston Scientific, Inc. may have application with the fibrotic lesion, but are potentially dangerous to adjacent areas of healthy vessel.

Figure 20A:
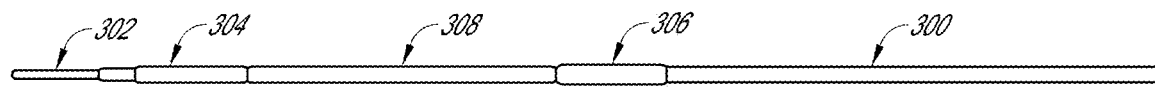
FIGS. 20A-20C are side elevational schematic views of dilatation catheters in accordance with the present invention.
Figure 20B:
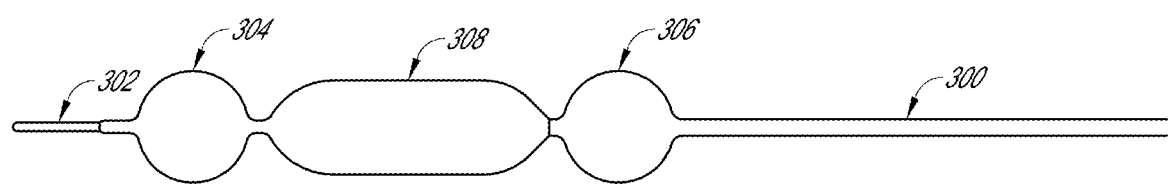
Figure 20C:
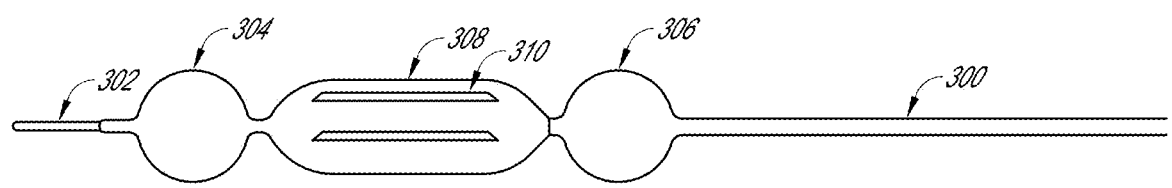

FIGS. 20A-20C show a dilatation device suitable for treatment of these lesions. FIG. 20A shows the device in a first, deflated condition employed when the device is being moved and positioned within the vasculature. FIG. 20B shows the device in its inflated condition employed when the lesion is being expanded. The device is constructed of an elongated shaft 300 having a lumen designated to allow a guidewire 302 to pass through. Mounted on the very distal end of the catheter is a first balloon 304 that is designated to be compliant and inflate at low pressures (i.e. less than 2 ATM). A second compliant balloon 306 is mounted proximally to the first balloon, and is also constructed to be compliant and inflate at similar pressures to the first balloon. A third balloon 308 is mounted between the first and second balloons, and is constructed to be non-compliant or semi-compliant that is capable of inflating to high pressures (i.e. 14-30 ATM). Optionally, the third balloon may have projecting structures 310 overlying it, or attached to its surface to act as stress-concentrators to allow the cutting or tearing of tissue in an predictable way during balloon inflation. The three balloons may communicate to a proximal hub or handle (not shown) independently for the purpose of inflation. Alternatively, one or more of the balloons may share an inflation lumen.

Figure 21A:
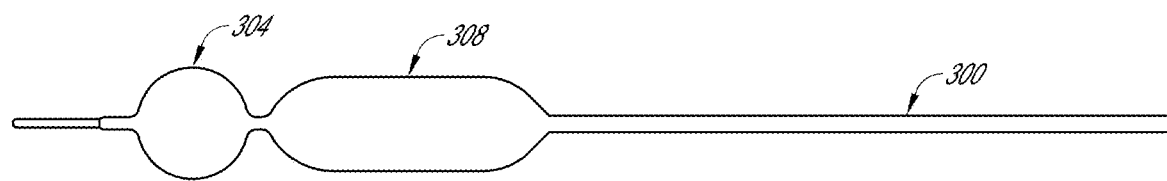
FIG. 21A-21D are side elevational views of components of an alternate dilatation catheter, in which the working length of a central balloon is adjustable by axially advancing or retracting a proximal balloon carried concentrically over the shaft for at least one distal balloon.
Figure 21B:
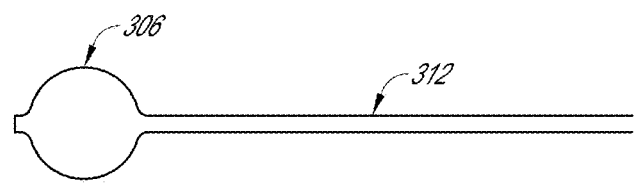
Figure 21C:
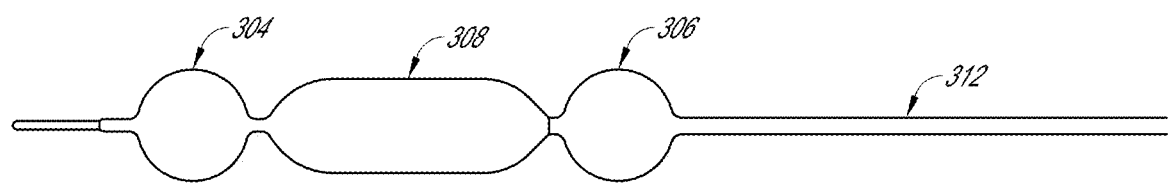
Figure 21D:
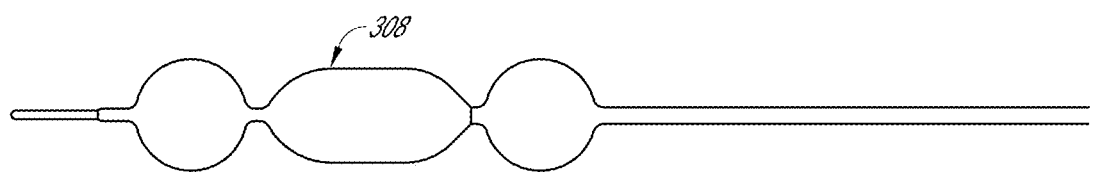

FIGS. 21A-21D show an alternative embodiment of the present device that has an adaptable second balloon length to match the lesion being treated. As shown in FIG. 31A, the device is composed of a first elongated shaft 300 having a first complaint balloon 304 and a non-compliant or semi-compliant balloon 308. These balloons communicate to a hub or handle via one or more inflation lumens contained within the first elongated shaft 300. As seen in FIG. 21B, the device further includes a second elongated shaft 312 upon which a second compliant balloon 306 is mounted. This second balloon communicates to the hub or handle via an inflation lumen contained within the second elongated shaft 312. As seen in FIG. 21C, the first shaft 300 is telescopically arranged within a lumen of a second shaft 312 so that they are moveable axially relative to each other. If a relatively long lesion is to be treated, the first and second shafts may be positioned so that the full length of the semi-compliant or non-compliant balloon 308 is capable of expansion as shown in FIG. 21C. Alternatively, if a shorter lesion is encountered, the second elongated shaft 312 can be distally advanced to partially cover the semi-complaint balloon or non-compliant balloon 308, limiting the length of the balloon that is available for expansion.

Figure 22:
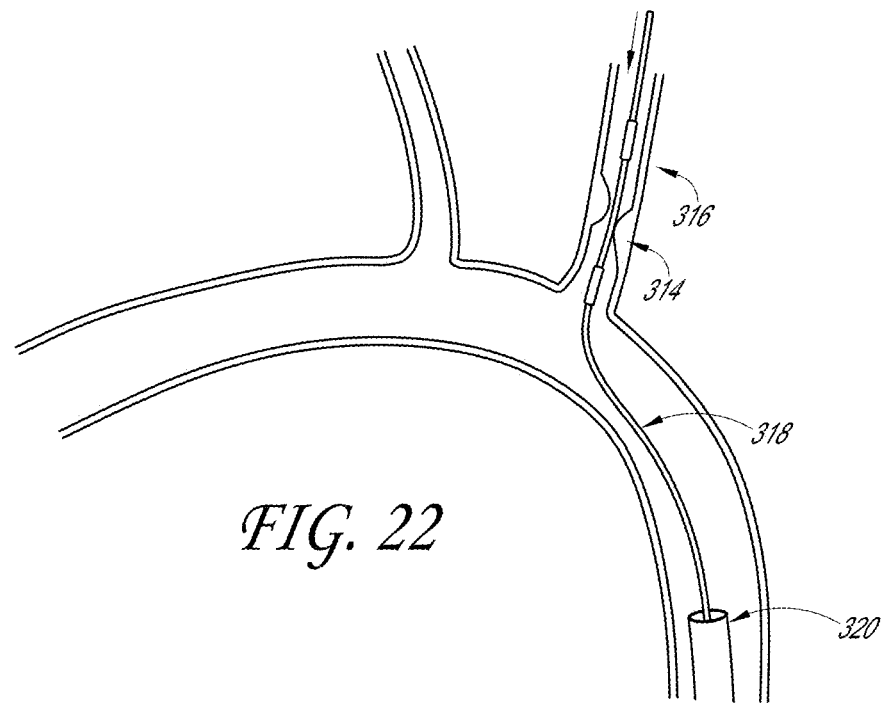
FIG. 22 illustrates the catheter placed across a stenosis.

FIG. 22 shows a stenosis 314 within a vein 316. The device 318 is tracked through the patient's vasculature through a sheath or guide catheter 320, and positioned so that the distal end of the catheter is near the stenosis.

Figure 23:
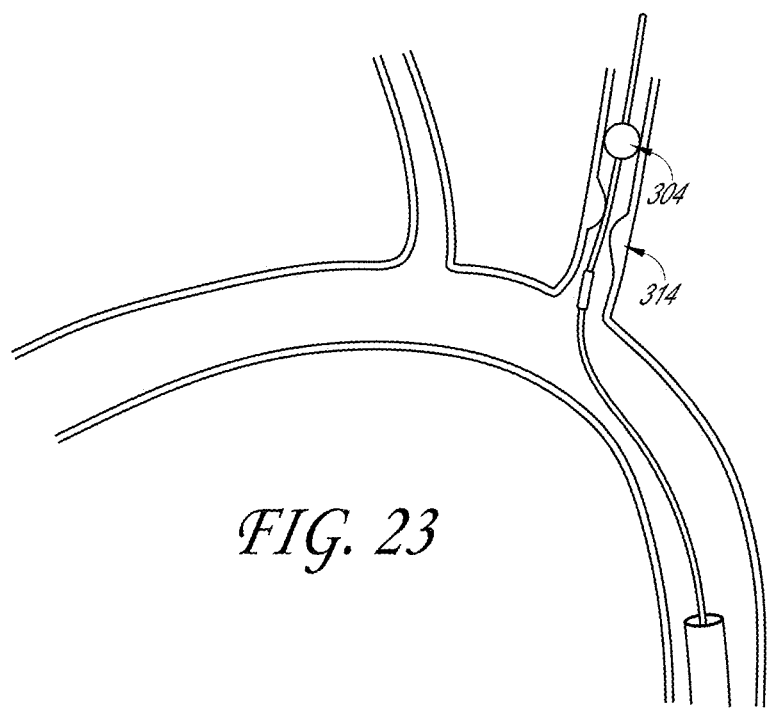
FIG. 23 illustrates the catheter of FIG. 22, with a distal balloon inflated within the vein.

Referring to FIG. 23, once the device is positioned within the vein, the first compliant balloon 304 is inflated and used to position the device relative to the stenosis 314. The balloon provides both visual and tactile feedback to the user regarding its position relative to the stenosis when observed under fluoroscopic guidance.

Figure 24:
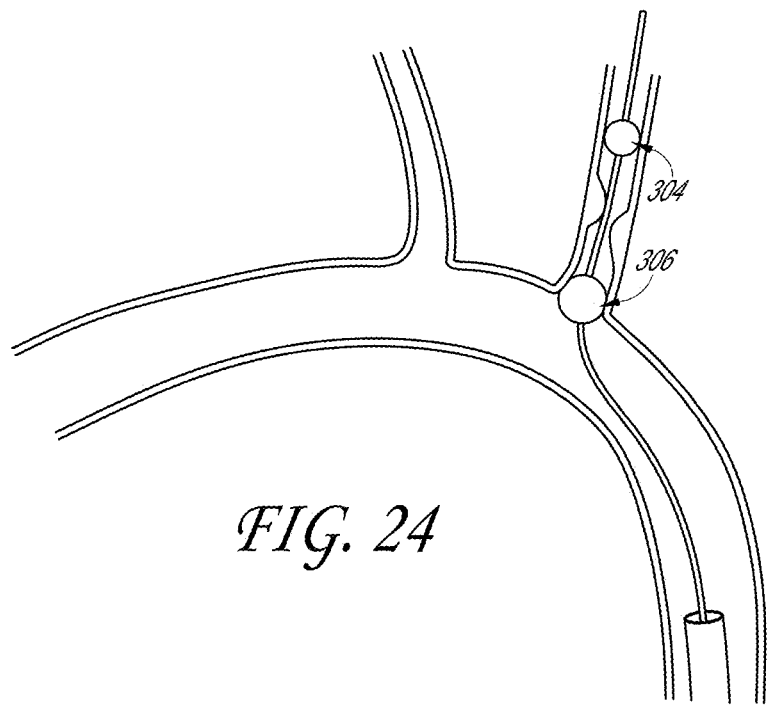
FIG. 24 is an illustration as in FIG. 23, with both a distal balloon and a proximal balloon inflated on opposing sides of a stenosis in a vein.

Referring to FIG. 24, with the first compliant balloon 304 in position, the second compliant balloon 306 is inflated and positioned relative to the opposite side of the lesion. If both compliant balloons are mounted to the same shaft, the lesion is centered between the two balloons. If the device is constructed as shown in FIG. 21, the first compliant balloon 304 is positioned optimally relative to the first side of the lesion, and then the second compliant balloon 306 is positioned optimally relative to the second side of the lesion. If the lesion is relatively short in length, the second shaft 312 may cover a portion of the semi-compliant or non-compliant balloon 308. Additionally, if stress-concentrating projections, e.g., wires, ridges or barbs, as shown in FIG. 20C are present, a portion of them may also be contained within the lumen of the second shaft 312.

Figure 25:
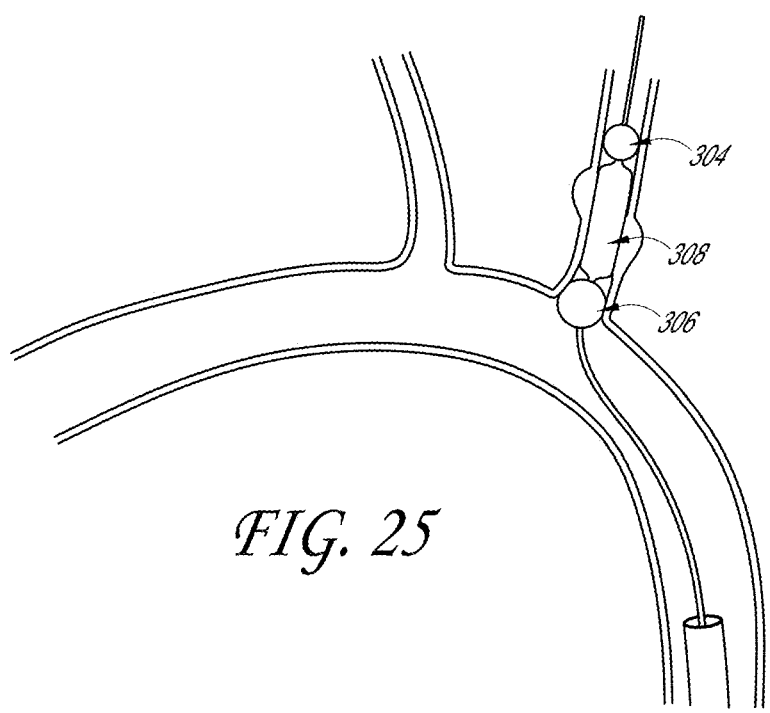
FIG. 25 is an illustration as in FIG. 24, with a central balloon expanded to dilate the stenosis.

With the compliant balloons inflated and optimally positioned, the semi-compliant or non-compliant balloon is inflated to dilate the stenosis. See FIG. 25. If the device is constructed as shown in FIG. 21, only the portion of the balloon that is not covered by the second elongated shaft will expand. Additionally, if the device has stress-concentrating structures 310 as seen FIG. 20C, they focus the expansion pressure and allow disruption of the lesion at lower pressures and with greater predictability.

Figure 26:
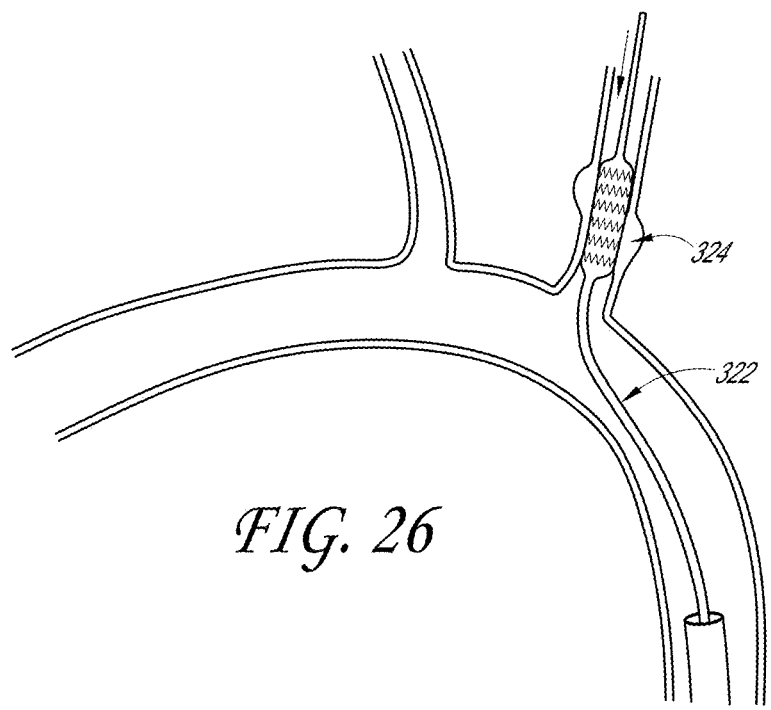
FIG. 26 illustrates a balloon expandable stent, carried by a balloon and expanded at a treatment site.

Once the lesion has been expanded with the balloon device described in FIGS. 20-25, a stent may be placed to maintain the expanded stenosis. See FIG. 26. The challenge with vessels typically encountered with the present procedure is that they are naturally large and compliant. After placement, there is a risk of the stent migrating or embolizing to the heart, which may be life-threatening to the patient. To address this risk, the stent is preferably designated to avoid stent migration after it has been implanted, as has been disclosed previously herein. This figure shows a balloon delivery catheter 322 delivering a balloon expandable stent 324.

Figure 27:
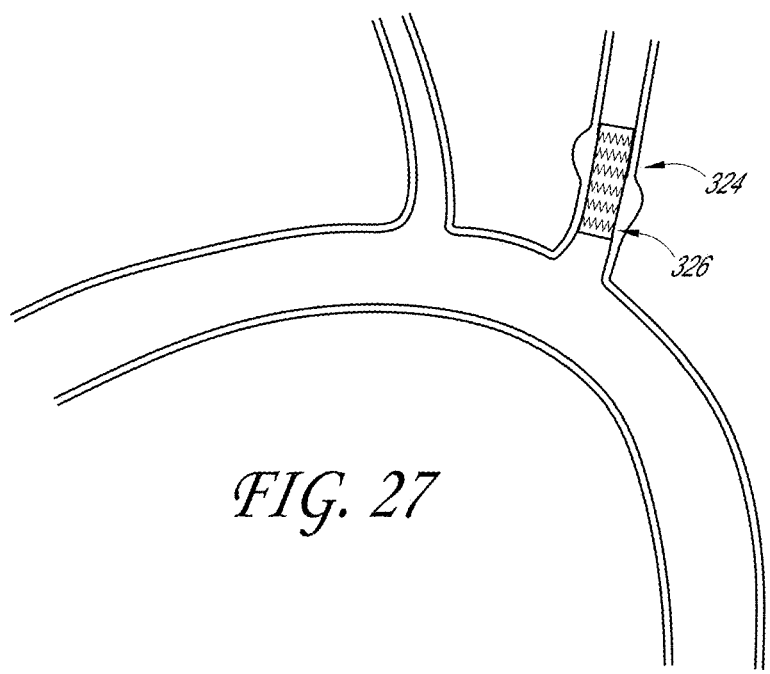
FIG. 27 illustrates the stent placed as shown in FIG. 26, with the dilatation balloon removed.

FIG. 27 shows the implanted stent. Typical stents are designed so that they maintain a smooth surface both in the expanded and unexpanded conditions. To avoid migration, this stent 324 is not smooth upon expansion, but instead has a plurality of wall engaging structures such as crowns 326 that point partially radially outward after the stent has been expanded. These crowns engage in the vessel wall and prevent migration.

Figure 28A:
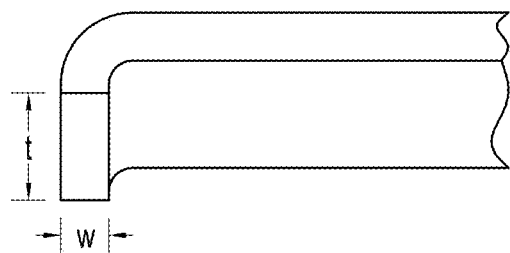
FIGS. 28A, 28C and 28D illustrate the relative dimensions of a conventional stent strut.
Figure 28B:
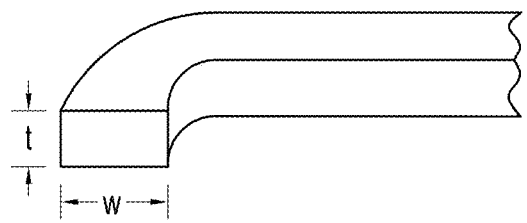
FIGS. 28B, 28E and 28F illustrate relative stent strut dimensions which enable the radially outwardly inclined apex shown in FIG. 28F.
Figure 28C:
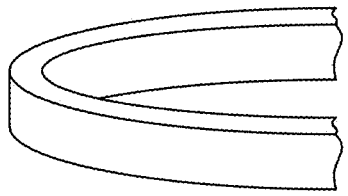
Figure 28E:
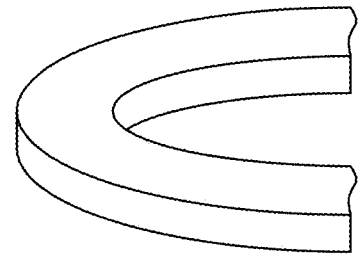
Figure 28D:
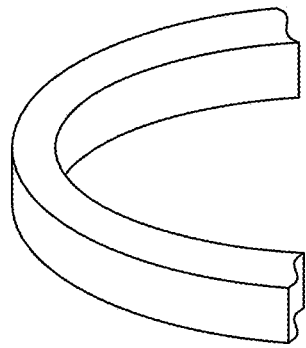
Figure 28F:
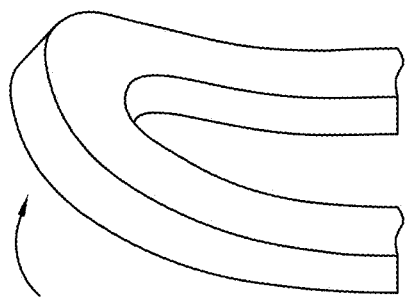

FIGS. 28A-28F show a stent design that creates crowns that point partially radially outward during stent expansion. FIG. 28A shows a typical stent design in that the stent thickness (t) is greater than its width (w). Upon expansion, crowns of this stent will remain smooth because it requires less energy to bend the width of the stent than its thickness as shown in FIGS. 28C & d. Alternatively, 28B shows the design of some of the crowns on the present stent, where the stent thickness (t') is less than its width (w') at the crown. Upon expansion, it requires more energy to bend purely in the stent width, resulting in a buckling effect, where the crown bends out of the surface of the stent and points partially radially outward as shown in FIG. 28F.

Figure 29:
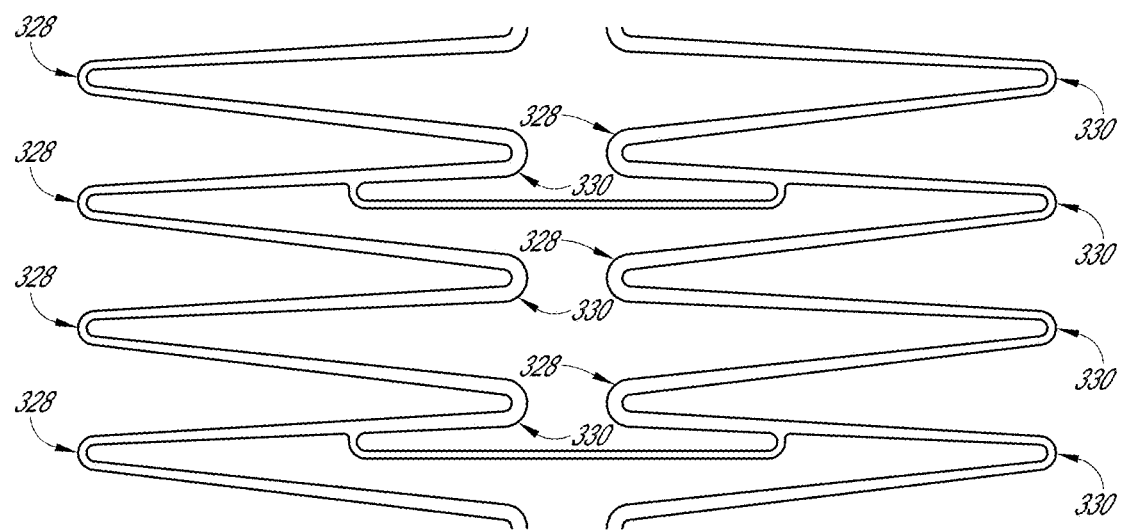
FIG. 29 is a plan view of a portion of a stent wall pattern in accordance with the present invention.

FIG. 29 shows a stent pattern that would create a stent that expands as discussed in connection with FIG. 27. The stent includes a first plurality of a first type of crown 328, where its thickness is greater than its width, resulting in a smooth crown after expansion. The stent includes a second plurality of a second type of crown 330, where its thickness is less than or equal to its width, resulting in a crown that points partially radially outward upon expansion. Both crown types are arranged within the stent pattern strategically, so that the first type of crown points away from the direction of potential migration, while the second type of crown points in the direction of potential migration. Upon expansion, the second type of crowns will expand outward to engage the vessel wall and prevent stent migration. In an alternative embodiment, (not shown) the second type of crowns may point away from the direction of potential migration as well. In a further alternative embodiment, not all crowns in a vertical row must be the same, but may alternate between crown types.

Figure 30:
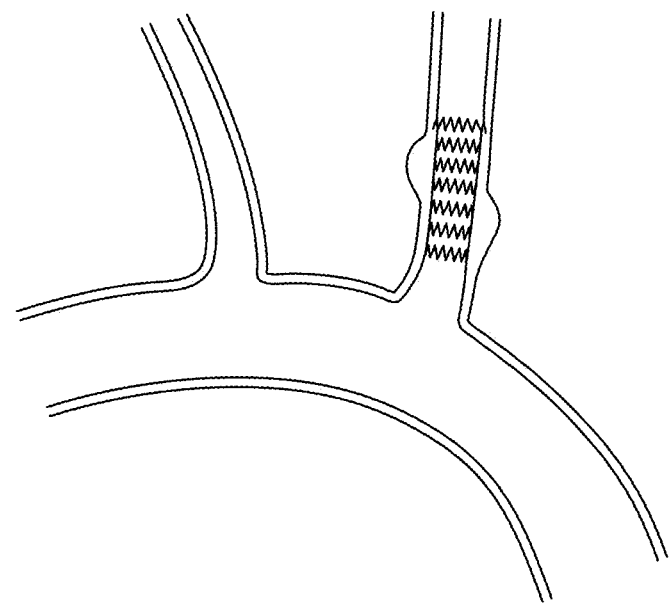
FIG. 30 illustrates a stent positioned across a treatment site, and having tissue engaging barbs to resist migration.

FIG. 30 shows an alternative embodiment of a stent having a plurality of tissue engaging small hooks or barbs on at least one end. These hooks engage the vessel wall and prevent stent migration. The hooks may be integrated into the pattern of the stent during fabrication, or may be added on after the stent is fabricated by bonding, welding, soldering and the like.

Although certain preferred embodiments and examples have been described herein, it will be understood by those skilled in the art that both the devices and methods of the present invention extend beyond the specifically disclosed examples to other alternative embodiments and/or uses of the invention and modifications and equivalents thereof. Thus, it is intended that the scope of the present inventive subject matter herein disclosed should not be limited by the particular disclosed embodiments described above, but should be determined by reference to the following claims.

What is claimed is:

1. A catheter, comprising:
a first elongate, tubular shaft, having an inflation lumen extending therethrough;
a first compliant balloon carried by the first shaft and a first non-compliant or semi-compliant balloon carried by the first shaft, wherein the first non-compliant or semi-compliant balloon is proximal to the first compliant balloon;
a second elongate, tubular shaft, having a central lumen, and axially movably carried by the first shaft, the central lumen having a distal opening;
a second compliant balloon carried by the second shaft, wherein the distal opening of the second shaft is axially movably positionable between a first position in which the first non-compliant or semi-compliant balloon is at least partially within the central lumen such that a limited length of the first non-compliant or semi-compliant balloon is expanded, and a second position in which the first non-compliant or semi-compliant balloon is fully expanded beyond the distal opening of the second shaft.

2. The catheter as in claim 1, wherein the first non-compliant or semi-compliant balloon is configured to be inflated between 14 ATM and 30 ATM.

3. The catheter as in claim 1, wherein the first compliant balloon and the second compliant balloon are configured to be inflated less than 2 ATM.

4. The catheter as in claim 1, wherein the first non-compliant or semi-compliant balloon comprises projections.

5. The catheter as in claim 1, wherein the first non-compliant or semi-compliant balloon comprises longitudinal ridges.

6. The catheter as in claim 1, wherein the first non-compliant or semi-compliant balloon comprises barbs.

7. The catheter as in claim 1, wherein the second compliant balloon is configured to provide visual and tactile feedback to the user regarding the position of the second compliant balloon relative to a stenosis when observed under fluoroscopic guidance.

8. The catheter as in claim 1, wherein a portion of projections of the first non-compliant or semi-compliant balloon are contained within the central lumen of the second shaft in the first position.

9. The catheter as in claim 1, wherein the first compliant balloon, the first non-compliant or semi-compliant balloon, and the second compliant balloon are configured to be inflated independently.

10. The catheter as in claim 1, wherein the first non-compliant or semi-compliant balloon comprises stress-concentrating structures configured to focus an expansion pressure to allow disruption of a lesion at lower pressures.

11. The catheter as in claim 1, further comprising a stent configured to maintain an expanded stenosis.

12. The catheter as in claim 11, wherein the stent comprises a plurality of wall engaging structures.

13. A catheter, comprising:
a first elongate, tubular shaft, having an inflation lumen extending therethrough;
a first balloon carried by the first shaft and a first variable length balloon carried by the first shaft, wherein the first variable length balloon is proximal to the first balloon;
a second elongate, tubular shaft, having a central lumen, and axially movably carried by the first shaft, the central lumen having a distal opening;
a second balloon carried by the second shaft,
wherein the distal opening of the second shaft is axially movably positionable between a first position in which the first variable length balloon is at least partially within the central lumen, and a second position in which the first variable length balloon is fully beyond the distal opening of the second shaft,
wherein the first variable length balloon is configured to be inflated with the distal opening in the first position, wherein the first variable length balloon comprises an adaptable length configured to match the lesion being treated.

14. The catheter as in claim 13, wherein the first variably length balloon is configured to be inflated with the distal opening in the second position.

15. The catheter as in claim 13, wherein the first variably length balloon comprises stress-concentrating structures configured to focus an expansion pressure to allow disruption of a lesion at lower pressures.

16. The catheter as in claim 13, further comprising a stent configured to maintain an expanded stenosis.

17. The catheter as in claim 16, wherein the stent comprises a plurality of wall engaging structures.

18. The catheter as in claim 17, wherein the plurality of wall engaging structures point partially radially outward after the stent expands.

19. The catheter as in claim 13, wherein the first balloon and the second balloon are compliant.

20. The catheter as in claim 13, wherein the first variable length balloon is non-compliant or semi-compliant.

* * * * *